United States Patent
Colman et al.

(10) Patent No.: US 9,044,565 B2
(45) Date of Patent: Jun. 2, 2015

(54) ORAL-NASAL CANNULA SYSTEM ENABLING CO2 AND BREATH FLOW MEASUREMENT

(75) Inventors: Joshua Lewis Colman, Jerusalem (IL); Gershon Levitsky, Jerusalem (IL)

(73) Assignee: Oridion Medical (1987) Ltd., Jerusalem (IL)

( * ) Notice: Subject to any disclaimer, the term of this patent is extended or adjusted under 35 U.S.C. 154(b) by 911 days.

(21) Appl. No.: 12/607,936

(22) Filed: Oct. 28, 2009

(65) Prior Publication Data
US 2010/0113955 A1    May 6, 2010

Related U.S. Application Data

(60) Provisional application No. 61/193,130, filed on Oct. 30, 2008.

(51) Int. Cl.
*A61M 16/06*    (2006.01)

(52) U.S. Cl.
CPC ... *A61M 16/0666* (2013.01); *A61M 2205/3334* (2013.01); *A61M 2210/0625* (2013.01); *A61M 2230/432* (2013.01); *A61M 16/0672* (2014.02)

(58) Field of Classification Search
CPC ............... A61M 16/0666; A61M 2205/3334; A61M 2210/0625; A61M 16/0672
USPC .......... 600/529, 531–532, 538–543; 128/203.29, 206.21–206.24, 207.18, 128/206.28, 207.16, 207.17
See application file for complete search history.

(56) References Cited

U.S. PATENT DOCUMENTS

| | | | |
|---|---|---|---|
| 759,152 A | 11/1904 | Bennett |
| 2,693,800 A | 11/1954 | Caldwell |
| 4,106,505 A | 8/1978 | Salter |
| 4,151,843 A | 5/1979 | Brekke |
| 4,156,426 A | 5/1979 | Gold |
| 4,263,908 A | 4/1981 | Mizerak |
| 4,367,735 A | 1/1983 | Dali |
| 4,422,456 A | 12/1983 | Tiep |
| 4,454,880 A | 6/1984 | Rudolph |
| 4,572,177 A | 2/1986 | Tiep |
| 5,046,491 A | 9/1991 | Derrick |

(Continued)

FOREIGN PATENT DOCUMENTS

| | | |
|---|---|---|
| EP | 1 849 491 A1 | 10/2007 |
| WO | 89/09565 A1 | 10/1989 |

(Continued)

OTHER PUBLICATIONS

European Search Report for European Patent Application No. 09174476.3 dated Mar. 2, 2010 (5 sheets).

(Continued)

*Primary Examiner* — Navin Natnithithadha
*Assistant Examiner* — Eric Messersmith
(74) *Attorney, Agent, or Firm* — Rodney J. Fuller; Booth Udall Fuller, PLC

(57) ABSTRACT

An oral-nasal cannula comprising at least one nasal breath inlet for carbon dioxide ($CO_2$) sampling; and at least one nasal breath inlet for flow measurement, wherein said at least one nasal breath inlet for flow measurement is separated from said at least one nasal breath inlet for $CO_2$ sampling, such that said cannula is configured to facilitate $CO_2$ sampling and flow measurement essentially without cross-interference.

11 Claims, 20 Drawing Sheets

(56) References Cited

U.S. PATENT DOCUMENTS

| | | | |
|---|---|---|---|
| 5,113,857 A | 5/1992 | Dickerman | |
| 5,199,421 A | 4/1993 | Figgiani | |
| 5,269,296 A | 12/1993 | Landis | |
| 5,269,496 A | 12/1993 | Schneider | |
| 5,335,656 A | 8/1994 | Bowe | |
| 5,375,593 A | 12/1994 | Press | |
| 5,495,848 A | 3/1996 | Aylsworth | |
| 5,740,799 A | 4/1998 | Nielsen | |
| 5,752,511 A | 5/1998 | Simmons | |
| 5,794,619 A | 8/1998 | Edelman | |
| 6,155,986 A * | 12/2000 | Brydon et al. | 600/538 |
| 6,379,312 B2 | 4/2002 | O'Toole | |
| 6,422,240 B1 | 7/2002 | Levitsky | |
| 6,439,234 B1 | 8/2002 | Curti | |
| 6,478,026 B1 | 11/2002 | Wood | |
| 6,533,983 B2 | 3/2003 | Curti | |
| 6,655,385 B1 | 12/2003 | Curti | |
| 6,837,238 B2 | 1/2005 | McDonald | |
| 6,913,017 B2 | 7/2005 | Roberts | |
| 6,938,619 B1 * | 9/2005 | Hickle | 128/207.18 |
| 7,007,694 B2 | 3/2006 | Aylsworth | |
| 7,337,780 B2 | 3/2008 | Curti | |
| 7,383,839 B2 | 6/2008 | Porat | |
| 2002/0124849 A1 | 9/2002 | De Villemeur | |
| 2003/0154987 A1 | 8/2003 | Palmer | |
| 2004/0206907 A1 | 10/2004 | Yamamori | |
| 2006/0042636 A1 * | 3/2006 | Nalagatla et al. | 128/207.18 |
| 2006/0174886 A1 * | 8/2006 | Curti et al. | 128/206.11 |
| 2007/0113847 A1 * | 5/2007 | Acker et al. | 128/204.18 |
| 2007/0272247 A1 | 11/2007 | Porat | |
| 2007/0277823 A1 * | 12/2007 | Al-Ali et al. | 128/204.18 |
| 2008/0190436 A1 * | 8/2008 | Jaffe et al. | 128/207.18 |

FOREIGN PATENT DOCUMENTS

| | | |
|---|---|---|
| WO | 95/17220 A1 | 6/1995 |
| WO | 01/95971 A1 | 12/2001 |
| WO | 03/068301 A1 | 8/2003 |
| WO | 2007/063532 A1 | 6/2007 |

OTHER PUBLICATIONS

Woda R. P. et al., "Cost-Benefit Analysis of Nasal Cannulae in Non-Tracheally Intubated Subjects", Anesth Analg, 82:506-510 (1996).

Oridion Medical 1987 Ltd., Microcap/Microcap Plus (Feb. 18, 2007).

* cited by examiner

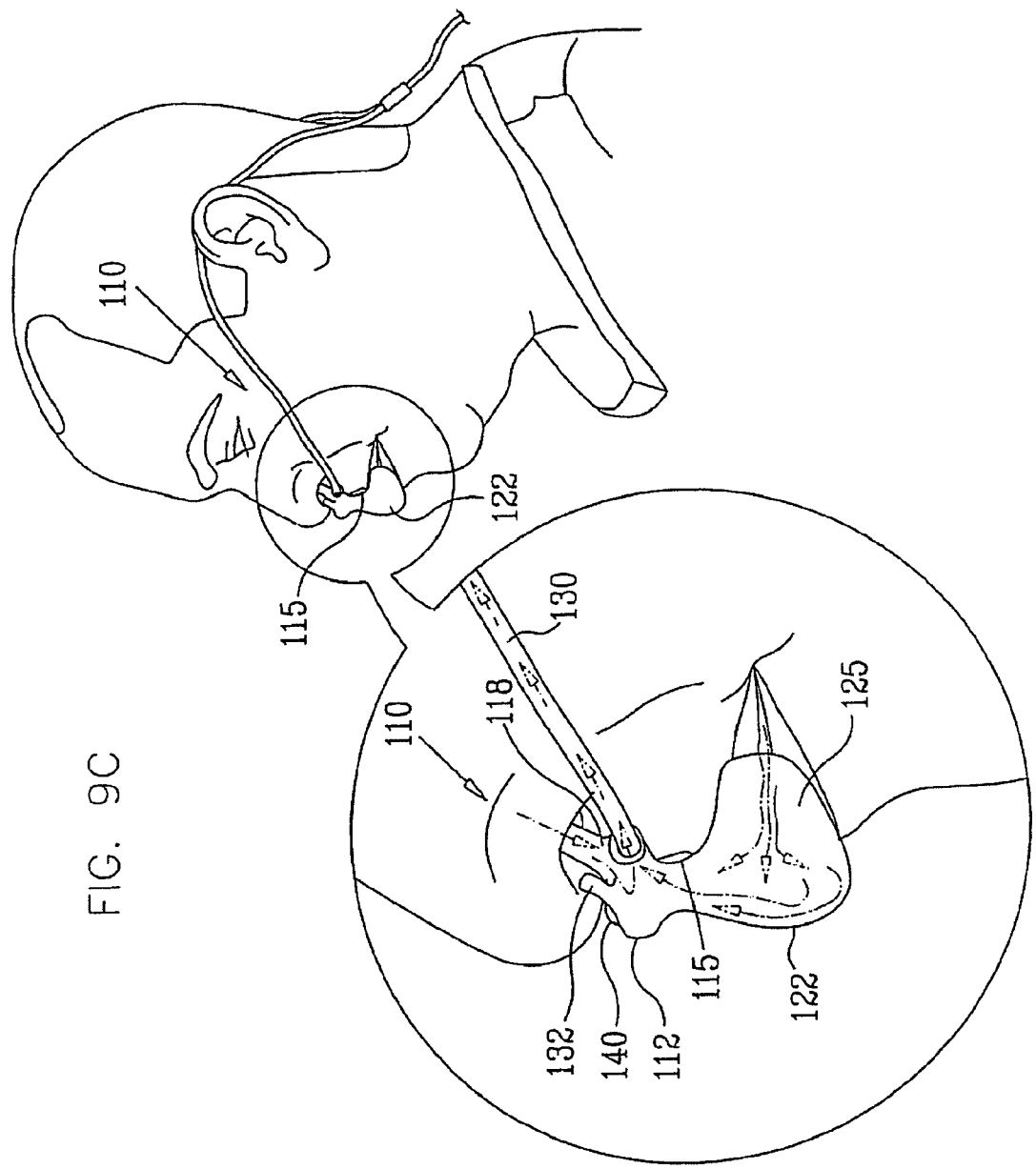

ORAL-NASAL CANNULA SYSTEM ENABLING CO2 AND BREATH FLOW MEASUREMENT

CROSS REFERENCE TO RELATED APPLICATIONS

This application claims the benefit of U.S. Provisional Patent Application No. 61/193,130, entitled "Oral-Nasal Cannula System Enabling $CO_2$ and Breath Flow Measurement", filed on Oct. 30, 2008 with the United States Patent and Trademark Office, the entirety of which is incorporated herein by reference.

FIELD OF THE INVENTION

Embodiments of the disclosure relate to an oral-nasal cannula system which enables $CO_2$ and breath flow measurement.

BACKGROUND OF THE INVENTION

In sleep labs, where patients are diagnosed for sleep disorders such as OSA (Obstructive Sleep Disorder), breath flow monitors are commonly used to recognize apnea events—periods where there is a loss of the patient's breath, as well as Hypopnea events—periods where there is a substantial reduction of the patient's tidal volume. These breath flow monitors often evaluate and display the patients breath flow characteristics using pressure or thermistor sensor technologies.

When using pressure sensor technologies, the patient is usually interfaced with a breath flow measurement cannula (nasal or oral/nasal) that is connected, at the instrument side, to a sensitive pressure sensor. Pressure changes detected are proportional to flow, and hence evaluation of the changing pressure felt along the cannula provides a breath flow pattern relative to the patient flow dynamics.

With thermistor technologies, an electronic line is used between the instrument and patient interface, and a thermistor is placed in proximity to the nose. The thermistor is sensitive to the flow of air passing across it, which creates slight changes in its temperature.

Despite the broad use of breath flow measurements, especially in sleep labs, usage of a flow meter alone to measure falls in tidal volume may be, in some situations, unreliable. First, a flow meter requires an oral-nasal cannula, since nasal alone would falsely define a hypopnic event when a patient would breath alternately between nose and mouth, and even when an oral nasal cannula is used, the strength of the flow pattern changes considerably when moving from nasal to oral breathing, which again can be picked up as a false hypopnic event. Second, movement of the cannula during the patient's sleep can also cause erroneous changes in the detected flow amplitude. Third, if the patient's mouth opens beyond a certain degree while asleep, the pressure created by the oral breathing is dispersed over the entire opening, thus decreasing the amount of pressure picked us by the flow meter (although generally, the larger the oral breath collection inlet is, the smaller the problem). Such occasions are very common in sleep labs, since patients who arrive at the sleep lab seeking diagnosis of a suspected Obstructive Sleep Apnea (OSA), tend to experience snoring as a symptom; snoring, in turn, usually occurs with an open mouth, and therefore may indirectly trigger a false hypopnic event.

In contrast to breath flow measurement, the concentration of carbon dioxide ($CO_2$) collected using an appropriate nasal or oral/nasal cannula and transported to a capnograph, is usually far less influenced from the position of the cannula or whether it is collected from the nose or the mouth. $CO_2$ level measurement, or "Capnography", is often defined as the measurement of the level of $CO_2$ in exhaled and/or inhaled breath. Since infrared light was found to be absorbed particularly well by $CO_2$, capnographs usually measure infrared absorption in the breath gasses, which indicates the level of $CO_2$ in these gasses. Other measurement technologies exist as well.

The information obtained from a capnographic measurement is sometimes presented as a series of waveforms, representing the partial pressure of $CO_2$ in the patient's exhaled breath as a function of time.

Clinicians commonly use capnography in order to assess a patient's ventilatory status. Respiratory arrest and shunt may be speedily diagnosed, and a whole range of other respiratory problems and conditions may be determined by the capnographic measurement. Capnography is considered to be a prerequisite for safe intubation and general anesthesia, and for correct ventilation management.

Sleep apnea is a disorder that commonly affects more than 12 million people in the United States. It takes its name from the Greek word apnea, which means "without breath." People with sleep apnea literally stop breathing repeatedly during their sleep, often for a minute or longer and as many as hundreds of times during a single night.

Sleep apnea can be caused by either complete obstruction of the airway (obstructive apnea) or partial obstruction (obstructive hypopnea—hypopnea is slow, shallow breathing), both of which can wake one up. There are three types of sleep apnea—obstructive, central, and mixed. Of these, obstructive sleep apnea (OSA) is the most common. OSA occurs in approximately 2 percent of women and 4 percent of men over the age of 35.

The exact cause of OSA remains unclear. The site of obstruction in most patients is the soft palate, extending to the region at the base of the tongue. There are no rigid structures, such as cartilage or bone, in this area to hold the airway open. During the day, muscles in the region keep the passage wide open. But as a person with OSA falls asleep, these muscles relax to a point where the airway collapses and becomes obstructed.

When the airway closes, breathing stops, and the sleeper awakens to open the airway. The arousal from sleep usually lasts only a few seconds, but brief arousals disrupt continuous sleep and prevent the person from reaching the deep stages of slumber, such as rapid eye movement (REM) sleep, which the body needs in order to rest and replenish its strength. Once normal breathing is restored, the person falls asleep only to repeat the cycle throughout the night.

Typically, the frequency of waking episodes is somewhere between 10 and 60. A person with severe OSA may have more than 100 waking episodes in a single night.

The primary risk factor for OSA is excessive weight gain. The accumulation of fat on the sides of the upper airway causes it to become narrow and predisposed to closure when the muscles relax. Age is another prominent risk factor. Loss of muscle mass is a common consequence of the aging process. If muscle mass decreases in the airway, it may be replaced with fat, leaving the airway narrow and soft. Men have a greater risk for OSA. Male hormones can cause structural changes in the upper airway.

Other predisposing factors associated with OSA include:
Anatomic abnormalities, such as a receding chin;
Enlarged tonsils and adenoids, the main causes of OSA in children;
Family history of OSA, although no genetic inheritance pattern has been proven;

Use of alcohol and sedative drugs, which relax the musculature in the surrounding upper airway;

Smoking, which can cause inflammation, swelling, and narrowing of the upper airway;

Hypothyroidism, acromegaly, amyloidosis, vocal cord paralysis, post-polio syndrome, neuromuscular disorders, Marfan's syndrome, and Down syndrome; and Nasal congestion.

The foregoing examples of the related art and limitations related therewith are intended to be illustrative and not exclusive. Other limitations of the related art will become apparent to those of skill in the art upon a reading of the specification and a study of the figures.

SUMMARY OF THE INVENTION

The following embodiments and aspects thereof are described and illustrated in conjunction with systems, tools and methods which are meant to be exemplary and illustrative, not limiting in scope.

There is provided, in accordance with an embodiment, an oral-nasal cannula comprising: at least one nasal breath inlet for carbon dioxide ($CO_2$) sampling; and at least one nasal breath inlet for flow measurement, wherein said at least one nasal breath inlet for flow measurement is separated from said at least one nasal breath inlet for $CO_2$ sampling, such that said cannula is configured to facilitate $CO_2$ sampling and flow measurement essentially without cross-interference.

In some embodiments, said at least one nasal breath inlet for $CO_2$ sampling comprises at least one nasal prong.

In some embodiments, said at least one nasal breath inlet for flow measurement comprises at least one nasal prong.

In some embodiments, the cannula further comprises at least one oral breath inlet for $CO_2$ sampling and for flow measurement.

In some embodiments, the cannula further comprises at least one oral breath inlet for $CO_2$ sampling and at least one oral breath inlet for flow measurement, wherein said at least one oral breath inlet for flow measurement is separated from said at least one oral breath inlet for $CO_2$ sampling.

In some embodiments, said at least one oral breath inlet for $CO_2$ sampling and at least one oral breath inlet for flow measurement are located within or in proximity to an oral scoop.

In some embodiments, said at least one oral breath inlet for $CO_2$ sampling is an oral breath collection bore positioned at an upper end of said scoop, and wherein said at least one oral breath inlet for flow measurement is a separate exit port.

In some embodiments, the cannula further comprises a mixture area being in flow connection with said at least one nasal breath inlet for $CO_2$ sampling and said at least one nasal breath inlet for flow measurement, wherein said mixture area is adapted to join gas flow from said at least one nasal breath inlet for $CO_2$ sampling and said at least one nasal breath inlet for flow measurement.

In some embodiments, said mixture area is further adapted to join gas flow from said at least one oral breath inlet and from said at least one nasal breath inlets for carbon dioxide ($CO_2$) sampling and flow measurement.

In some embodiments, the cannula further comprises a $CO_2$ sampling tube configured for connection to a capnograph, and a breath flow measurement tube configured for connection to a flow meter.

In some embodiments, the cannula further comprises an oxygen delivery outlet.

There is further provided, in accordance with an embodiment, an oral-nasal cannula system comprising: a $CO_2$ sampling sub-system; and a breath flow measurement sub-system, wherein said $CO_2$ sampling sub-system and said breath flow measurement sub-system are configured to operate independently, essentially without cross-interference.

In some embodiments, independent operation of said $CO_2$ sampling sub-system and said breath flow measurement sub-system is achieved by virtue of early separation of exhaled nasal breath for $CO_2$ sampling and exhaled nasal breath for flow measurement.

In some embodiments, the early separation of exhaled nasal breath is performed by having separate nasal breath inlets for $CO_2$ sampling and for flow measurement.

In some embodiments, said nasal breath inlets comprise nasal prongs.

In some embodiments, independent operation of said $CO_2$ sampling sub-system and said breath flow measurement sub-system is achieved by virtue of early separation of exhaled oral breath for $CO_2$ sampling and exhaled oral breath for flow measurement.

In some embodiments, the early separation of exhaled oral breath is performed by having separate oral breath inlets for $CO_2$ sampling and flow measurement.

In some embodiments, the separate oral breath inlets are located within or in proximity to an oral scoop.

In some embodiments, said at least one oral breath inlet for $CO_2$ sampling is an oral breath collection bore positioned at an upper end of said scoop, and wherein said at least one oral breath inlet for flow measurement is a separate exit port in said oral scoop.

In some embodiments, the oral-nasal cannula system further comprises a mixture area being in flow connection with said $CO_2$ sampling sub-system and said breath flow measurement sub-system, wherein said mixture area is configured to join gas flow from said $CO_2$ sampling sub-system and said breath flow measurement sub-system.

In some embodiments, the oral-nasal cannula system further comprises a $CO_2$ sampling tube adapted to be connected to a capnograph, and a breath flow measurement tube adapted to be connected to a flow meter.

In some embodiments, the oral-nasal cannula system further comprises an oxygen delivery sub-system adapted to operate independently, essentially without interfering with operation of said $CO_2$ sampling sub-system and said breath flow measurement sub-system.

In some embodiments, the oral-nasal cannula system further comprises a capnograph connected to said $CO_2$ sampling sub-system.

In some embodiments, the oral-nasal cannula system further comprises a flow meter connected to said breath flow measurement sub-system.

There is further provided, in accordance with an embodiment, a method for sampling $CO_2$ and measuring breath flow, essentially without cross-interference, the method comprising: sampling breath for $CO_2$ analysis from at least one nasal breath inlet of an oral-nasal cannula; and collecting breath for breath flow measurement from at least one nasal inlet of the oral-nasal cannula, wherein said at least one nasal breath inlet for flow measurement is separated from said at least one nasal breath inlet for $CO_2$ sampling, such that sampling $CO_2$ and measuring breath flow are essentially not cross-interfering.

In some embodiments, the method further comprises joining gas flow from the at least one nasal breath inlet for $CO_2$ sampling and said at least one nasal breath inlet for flow measurement.

In some embodiments, the method further comprises splitting the joined gas flow into two separate tubes: a $CO_2$ sampling tube adapted to be connected to a capnograph, and a breath flow measurement tube adapted to be connected to a flow meter.

In some embodiments, the sampling for $CO_2$ analysis and the collecting for breath flow measurement are being conducted simultaneously.

In addition to the exemplary aspects and embodiments described above, further aspects and embodiments will become apparent by reference to the figures and by study of the following detailed description.

BRIEF DESCRIPTION OF THE FIGURES

Exemplary embodiments are illustrated in referenced figures. Dimensions of components and features shown in the figures are generally chosen for convenience and clarity of presentation and are not necessarily shown to scale. It is intended that the embodiments and figures disclosed herein are to be considered illustrative rather than restrictive. The figures are listed below.

FIGS. 3A, 3B and 3C are schematic illustrations of gas flow in the oral nasal sampling cannula of FIGS. 1A-2C, wherein FIG. 3A depicts oxygen flow and FIGS. 3B and 3C depict sampling of exhaled breath;

FIGS. 6A, 6B and 6C are schematic illustrations of gas flow in the oral nasal sampling cannula of FIGS. 4A-5C, wherein FIG. 6A depicts oxygen flow and FIGS. 6B and 6C depict sampling of exhaled breath;

FIGS. 9A, 9B and 9C are schematic illustrations of gas flow in the oral nasal sampling cannula of FIGS. 7A-8C, wherein FIG. 9A depicts oxygen flow and FIGS. 9B and 9C depict sampling of exhaled breath;

DETAILED DESCRIPTION OF THE PREFERRED EMBODIMENT

An aspect of some embodiments relates to an oral-nasal cannula system which includes a $CO_2$ sampling sub-system and a breath flow measurement sub-system which are configured to operate independently, essentially without cross-interference.

The $CO_2$ sampling sub-system is optionally based on the oral-nasal cannula system for $CO_2$ sampling disclosed in U.S. Patent Application Publication No. 2007/0272247 (hereinafter "the '247 publication").

The present disclosure implements a breath flow measurement sub-system into the oral-nasal cannula system of the '247 publication, in an advantageous way that enables $CO_2$ and breath flow measurement with essentially no cross-interference.

The Oral-Nasal Cannula System of the '247 Publication

Figure 1A:
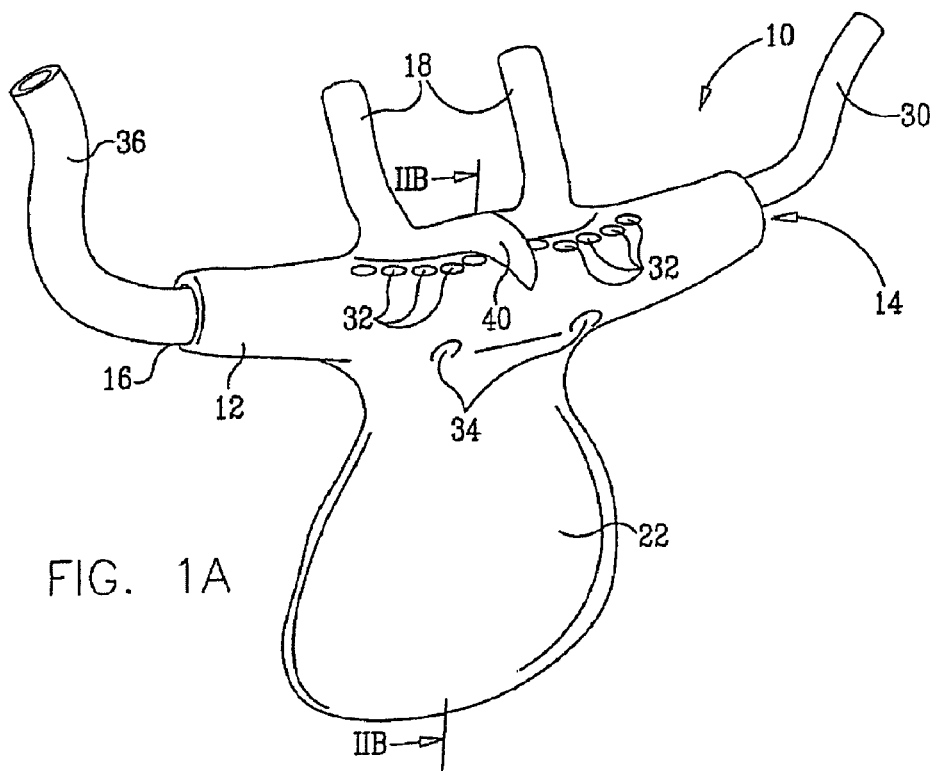
FIG. 1A is a simplified front-view pictorial illustration of an oral nasal sampling cannula.
Figure 1B:
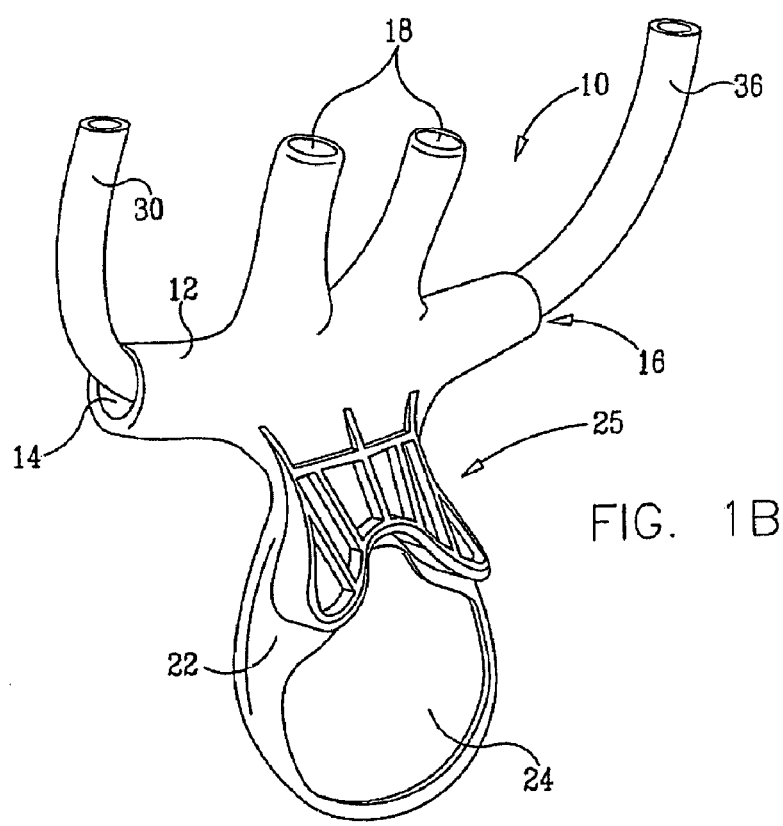
FIGS. 1B and 1C are simplified rear-views pictorial illustrations of an oral nasal sampling cannula.
Figure 1C:
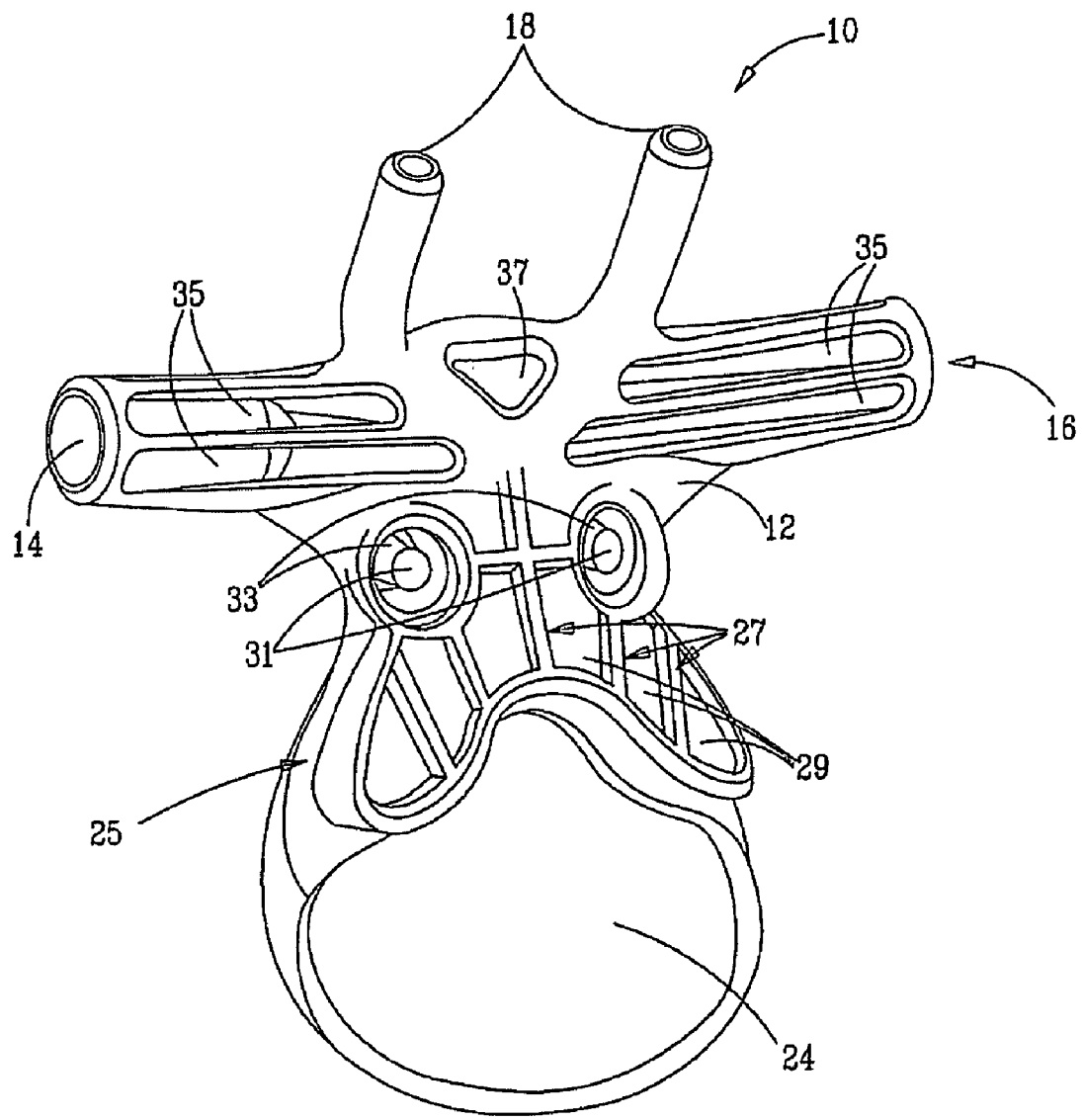
Figure 2A:
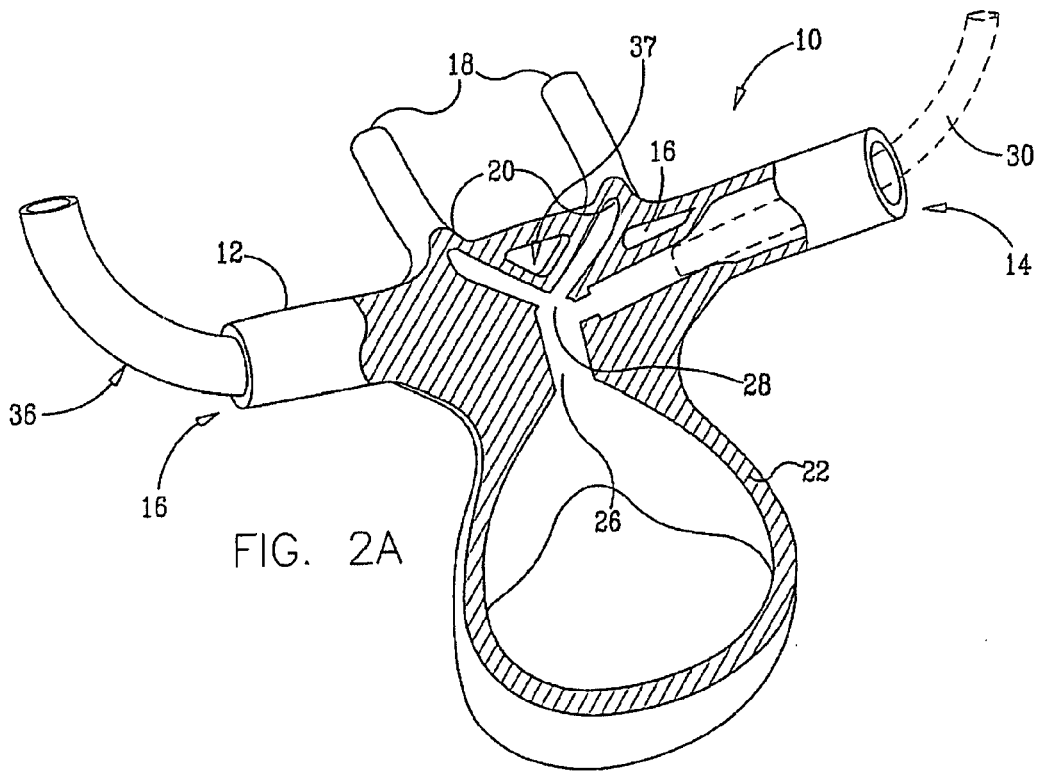
FIGS. 2A and 2B and 2C are partial perspective illustrations with simplified sectional illustrations taken along section lines: IIA-IIA (in FIG. 2B, the line IIA-IIA is taken on the whole part), IIB-IIB (in FIG. 1A) and IIC-IIC (in FIG. 2B, the line IIC-IIC is taken on the whole part)
Figure 2B:
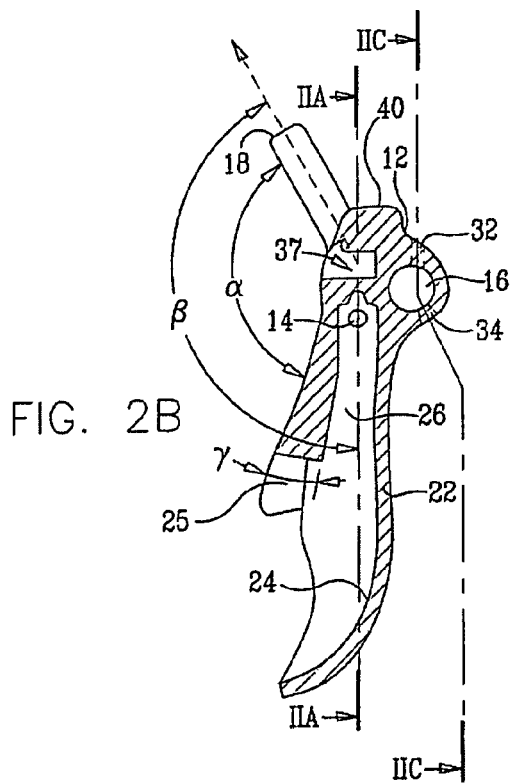
Figure 2C:
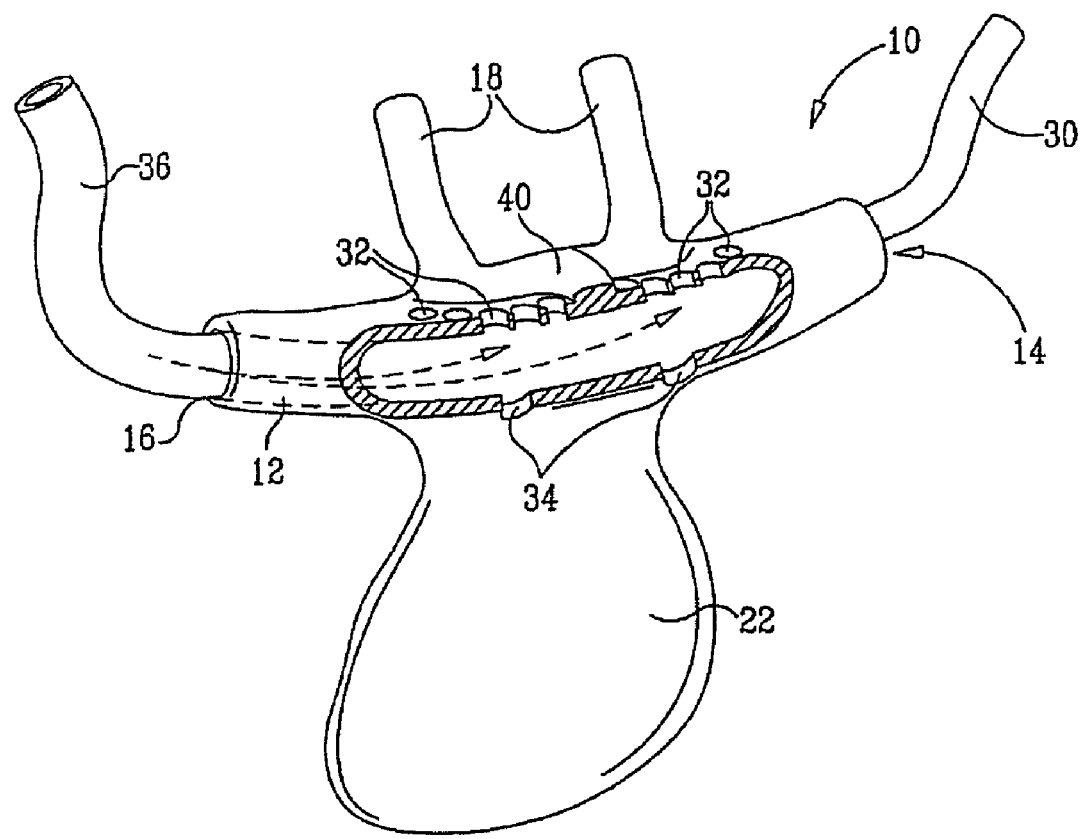

Reference is now made to FIGS. 1A-2C. FIG. 1A is a simplified front-view pictorial illustration of an oral nasal sampling cannula constructed and operative in accordance with an embodiment of the present disclosure. FIGS. 1B and 1C are simplified rear-views pictorial illustrations of an oral nasal sampling cannula constructed and operative in accordance with an embodiment. FIGS. 2A, 2B and 2C are simplified sectional illustrations taken along section lines: IIA-IIA (in FIG. 2B), IIB-IIB (in FIG. 1A) and IIC-IIC (in FIG. 2B). FIGS. 1A-2C show an oral nasal sampling cannula 10, which is adapted for collection of gases, such as carbon dioxide, exhaled by a subject, and for supplying oxygen to the subject. The oral nasal sampling cannula 10 is adapted to sample orally, nasally exhaled breath, or both.

The oral nasal sampling cannula 10 comprises a main body portion 12, having formed therein an exhaled breath collection bore 14 and an oxygen delivery bore 16. A pair of hollow nasal prongs 18, having inner ends 20 which are in fluid flow communication with a pair of nasal breath collection bores 21, is adapted for at least partial insertion into the nostrils of the subject and may be integrally formed with the main body portion 12.

An oral scoop element 22, including an internal surface 24, a spacer, formed in the shape of a wedge 25 adapted to maintain a minimum distance between a portion of an oral cavity and a portion of the oral scoop 22. The surface of the wedge 25 may be non-smooth, contoured and/or include structural elements such as rigids, holes, bars, nibs and the like, to form additional structural rigidity, to allow fixed seating against the face (for example, the lip), to allow moisture (for example, sweat) evaporation, to allow fixed seating against the face for subjects having facial hair, to provide comfort and/or to avoid sliding (for example, lateral sliding) of the oral nasal sampling cannula 10 on the face of the subject being examined. FIG. 1B shows examples of rigids 27 that may form spaces 29 between them. FIG. 1C shows examples of rigids 27 that may form spaces 29 between them, holes 33 that may have pins 31 extending all the way or part of the way through them, hole 37 (also shown in 2A and 2B), spaces 35 or any other element. The oral scoop element 22 may be integrally formed with main body portion 12. The oral scoop element 22 terminates at a top portion thereof in an oral breath collection bore 26 (FIGS. 2A and 2B), which is in fluid flow connection with nasal breath collection bores 21, thereby forming an essentially single junction 28 (FIG. 2A). The junction can also be located closer to one prong 18 than to the other. The junction can also be located above the position shown in FIG. 2A or in any other place that would allow the desired fluid flow. FIG. 2C shows the space 15 extending from the oxygen delivery bore 16, which is in fluid flow communication with an oxygen delivery tube 36, and exits the oral nasal sampling cannula at nasal and oral oxygen delivery openings 32 and 34, toward the nose and mouth of the subject.

Single junction 28 is in fluid flow communication with exhaled breath collection bore 14, which in turn is in fluid flow communication with an exhaled breath collection tube 30, which is adapted to be connected to a suctioning pump, such as that used in a side-stream capnograph (not shown), for example Microcap®, which is commercially available from Oridion Jerusalem, Israel.

Main body portion 12 includes, optionally at a forward facing surface thereof or alternatively at any other suitable location, nasal oxygen delivery openings 32 and may optionally also include oral oxygen delivery openings 34, both nasal and oral oxygen delivery openings being in fluid flow communication with oxygen delivery bore 16, as seen with particular clarity in FIG. 2B. Oxygen delivery bore 16 is in fluid flow communication with an oxygen delivery tube 36, which is adapted to be connected to a source of oxygen (not shown).

The hatch lines may refer to one or more material(s) including silicon, rubber, plastic, other polymeric material, metal, glass or any other material(s).

Oxygen delivery tube 36 and exhaled breath collection tube 30 may optionally be placed around the ears of the subject, thereby stabilizing the oral nasal sampling cannula 10 on the subject's face.

As seen clearly in FIG. 1A, a separator 40 is integrally formed with main body portion 12 at a forward facing surface thereof. Separator 40 is adapted to engage the nose of the subject, thereby distancing the nose from nasal oxygen delivery openings 32 and ensuring that a sufficient oxygen supply reaches the subject's nose, while not closing off the subject's nasal opening, which would incur a resistance to air flow during exhalation.

FIG. 2B, which is a sectional illustration taken along section line IIB-IIB in FIG. 1A clearly shows the wedge 25, which is structured maintain a minimum distance between the subject's face (for example, the upper lip) and a portion of the oral scoop 22.

Optionally, the oral nasal sampling cannula 10 is suited to the structure of a human face by having an angle, indicated by the letter a in FIG. 2B, between at least one nasal prong 18 and oral scoop element 22. The cannula may be structured with an angle between the axis of revolution of the interior part of the oral breath collection bore 26 and the axis of revolution of the interior part of at least one nasal prong 18 (this angle is indicated by the letter 13). The cannula structured with a certain angle β may allow a desirable flow of the fluid being sampled.

Figure 3A:
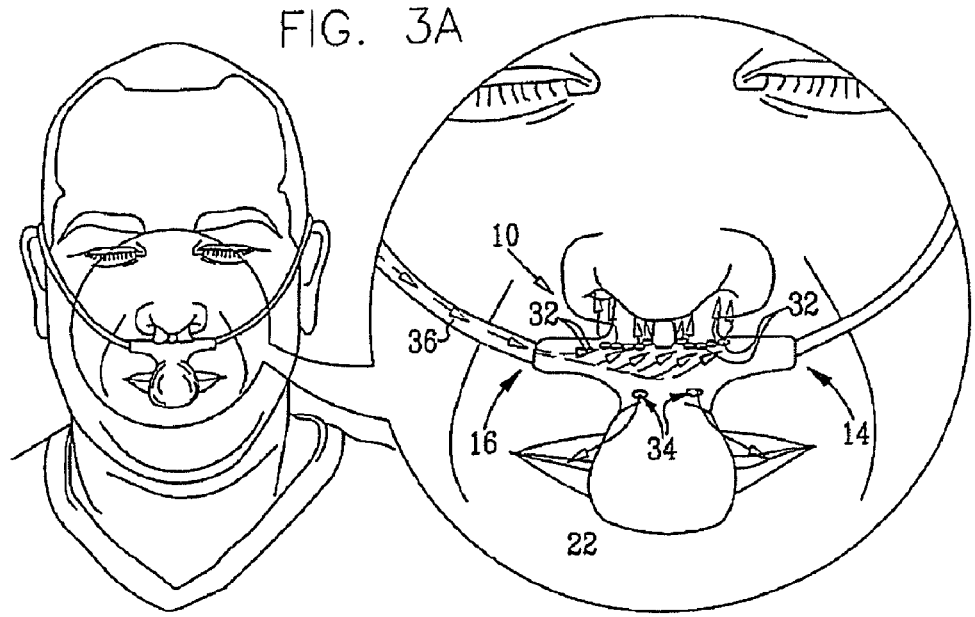
Figure 3B:
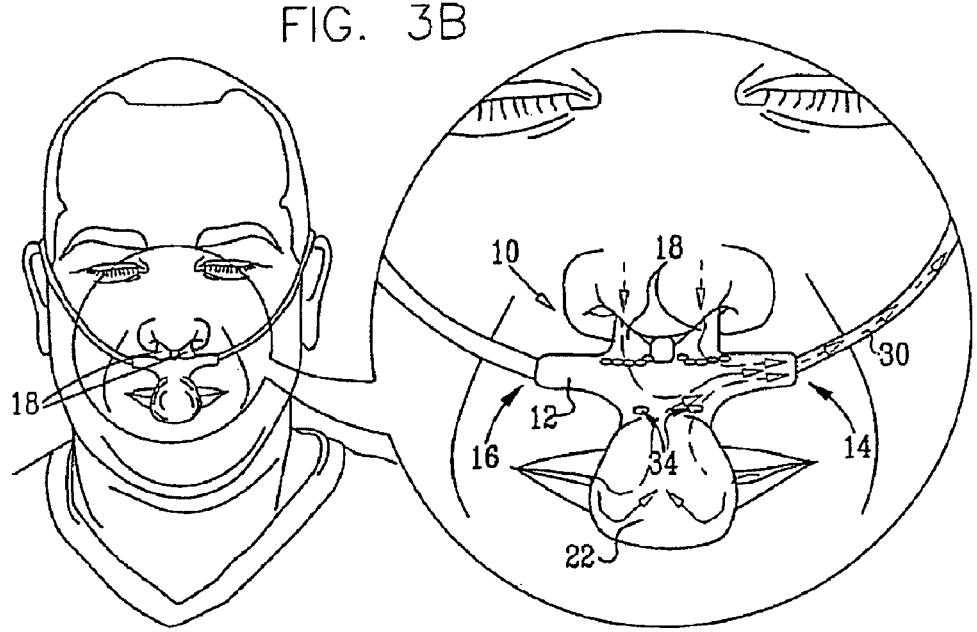
Figure 3C:
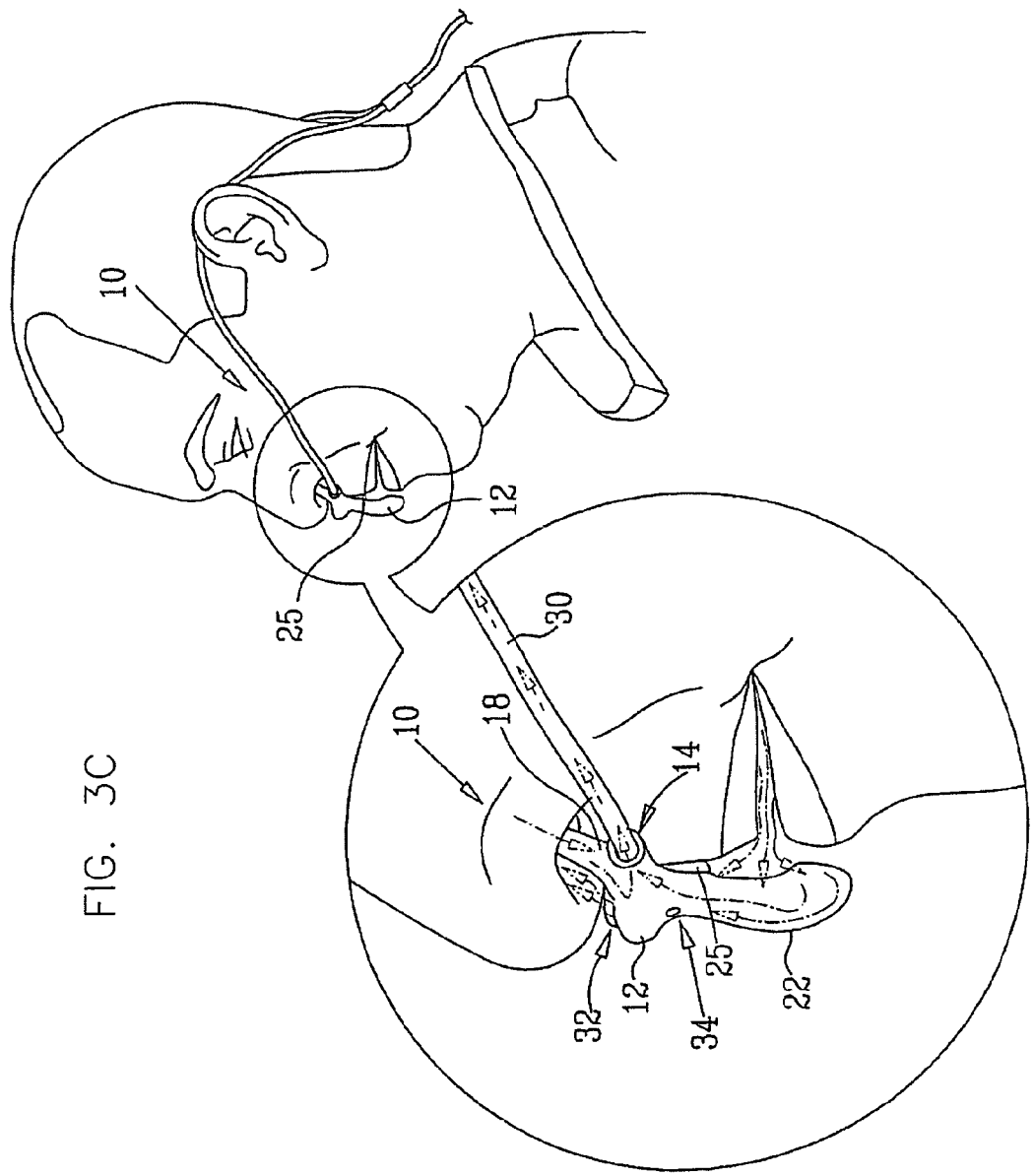

Reference is now made to FIGS. 3A, 3B and 3C, which are schematic illustrations of gas flow in the oral nasal sampling cannula of FIGS. 1A-2C, wherein FIG. 3A depicts oxygen flow and FIGS. 3B and 3C depict sampling of exhaled breath.

As seen in FIG. 3A, oxygen from an oxygen source (not shown) flows through oxygen delivery tube 36, through oxygen delivery bore 16 (FIG. 2B) and exits the oral nasal sampling cannula at nasal and oral oxygen delivery openings 32 and 34, toward the nose and mouth of the subject. Oral oxygen delivery openings 34 are slightly slanted, to ensure that emitted oxygen will be directed to the mouth of the subject at least partially around the oral scoop element 22.

Turning to FIG. 3B, it is seen that breath exhaled through the subject's nose is directed through nasal prongs 18 and nasal breath collection bores 21 (FIG. 2A) toward exhaled breath collection bore 14 (FIG. 2A). In a similar manner, breath exhaled through the subject's mouth is collected in oral scoop element 22, and is directed through oral breath collection bore 26 (FIG. 2B) to exhaled breath collection bore 14. All the exhaled breath collected in exhaled breath collection bore 14 flows into exhaled breath collection tube 30, typically by means of negative pressure supplied by a pumping element (not shown), which may be connected to exhaled breath collection tube 30.

FIG. 3C shows the aerodynamic nature of internal surface 24 (FIG. 1B) of oral scoop element 22. As seen in FIG. 3C, breath exhaled from the subject's mouth hits different points on the internal surface 24 of oral scoop element 22. The multiple different flow surfaces of internal surface 24 ensure that all the exhaled breath that reaches internal surface 24 will be directed toward oral breath collection bore 26 (FIG. 2B). Also shown in FIG. 3C is the wedge 25 that allows increasing the gap between the oral scoop element 22 and the subject's mouth and thus prevents the suction of the oral scoop element 22 into the subject's mouth.

It is appreciated that the importance of the use of several nasal oxygen delivery openings 32 is that during exhalation, which is the period at which the subject's exhaled breath is sampled, it is crucial that the sampled breath is substantially not diluted by the oxygen that is being delivered. In the oral nasal sampling cannula 10, the positive pressure caused by the exhalation is used to push away at least most of the oxygen from the direction of the nostril, thereby ensuring that the majority of the oxygen is not sucked into the nasal prongs 18 and does not dilute the sampled breath. The use of several nasal oxygen delivery openings 32 spreads out the pressure of the oxygen flow, and thus the exhaled air is at an even larger positive pressure relative to the pressure of the oxygen exiting each delivery opening 32, thus more effectively pushing away the oxygen.

It is appreciated that the importance of the use of an oral scoop element is in the fact that a larger percentage of the orally exhaled breath is collected and eventually reaches the sample analysis element. This feature is especially important when monitoring the breath of heavily sedated subjects, which tend to breathe through an open mouth and to have a very low breath rate, typically fewer than 10 breaths per minute, as opposed to greater than 12 breaths per minute in a non-sedated subject. Additionally, the collection of all the exhaled breath from oral scoop element 22 into the oral breath collection bore 26, which is substantially narrower than oral scoop element 22, amplifies the pressure of the orally exhaled breath, which is typically very low, specifically in sedated subjects.

Moreover, amplification of the pressure of orally exhaled breath is important for the accuracy of the sampling due to the fact that the pressure created during exhalation at the exit of a mouth which is wide open is much lower than the pressure created by the flow of exhaled breath via the nostrils.

It is also appreciated that the sampled exhaled breath is substantially not diluted by ambient air due to pressure gradients within the system, and a majority of the sampled exhaled breath does not escape from the system.

If the subject is performing oral and nasal breathing, there may be slightly higher pressure in nasal breath collection bores 21 (FIG. 2A) and in oral breath collection bore 26 (FIG. 2B), and a slightly more negative pressure in exhaled breath collection bore 14 (FIGS. 1B-2B) due to the suctioning pump which is connected to exhaled breath collection tube 30, thereby ensuring that the exhaled breath is removed from the oral nasal sampling cannula 10 and is preferably transported towards a capnograph. Due to the relatively higher pressure within the oral scoop element 22, essentially no ambient air enters breath collection bores 21 and 26 and the exhaled breath is substantially not diluted. In the case of nasal breath only, the air in oral scoop element 22 is of the same pressure as the air all around it, whereas there is a slightly higher pressure in the nasal breath collection bores 21 pushing down via the single junction 28 (FIG. 2A), to create a relatively positive pressure at the oral breath collection bore 26, thereby ensuring that essentially no ambient air will enter the oral nasal sampling cannula 10. Additionally, essentially a majority of the exhaled breath does not escape the system due to the pumping element that constantly creates a relatively negative pressure in exhaled breath collection bore 14, thereby ensuring that a sufficient amount of the exhaled breath will travel toward the exhaled breath collection tube 30 and not out toward the ambient air.

In a similar manner, in the case of oral breath only, the air in nasal prongs 18 and in nasal breath collection bores 21 is of the same pressure as the air all around it, whereas there is a slightly higher pressure in the oral breath collection bore 26 pushing up via the single junction 28 (FIG. 2A), to create a relatively positive pressure at the nasal breath collection bores 21, thereby ensuring that essentially no ambient air will enter the system. Additionally, essentially a sufficient amount of exhaled breath does not escape the system due to the pumping element that constantly creates a relatively negative pressure in exhaled breath collection bore 26, thereby ensuring that essentially most of the exhaled breath will travel toward the exhaled breath collection tube 30 and not out toward the ambient air.

Figure 4A:
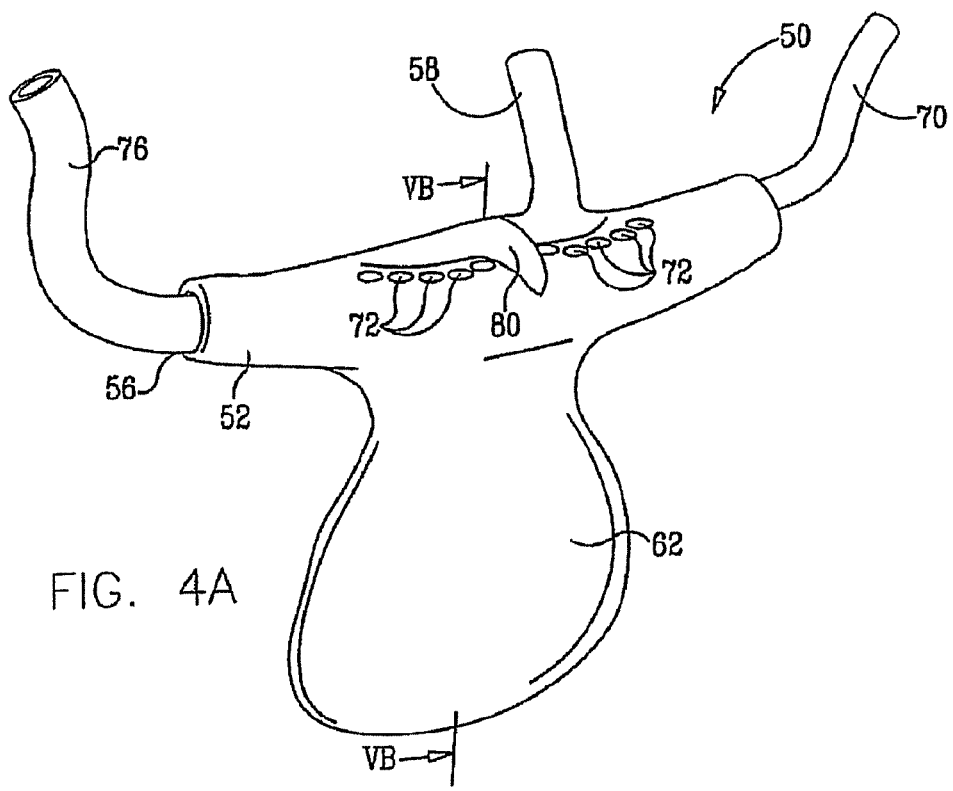
FIGS. 4A and 4B are simplified front-view and rear-view pictorial illustrations of an oral nasal sampling cannula having a single nasal prong.
Figure 4B:
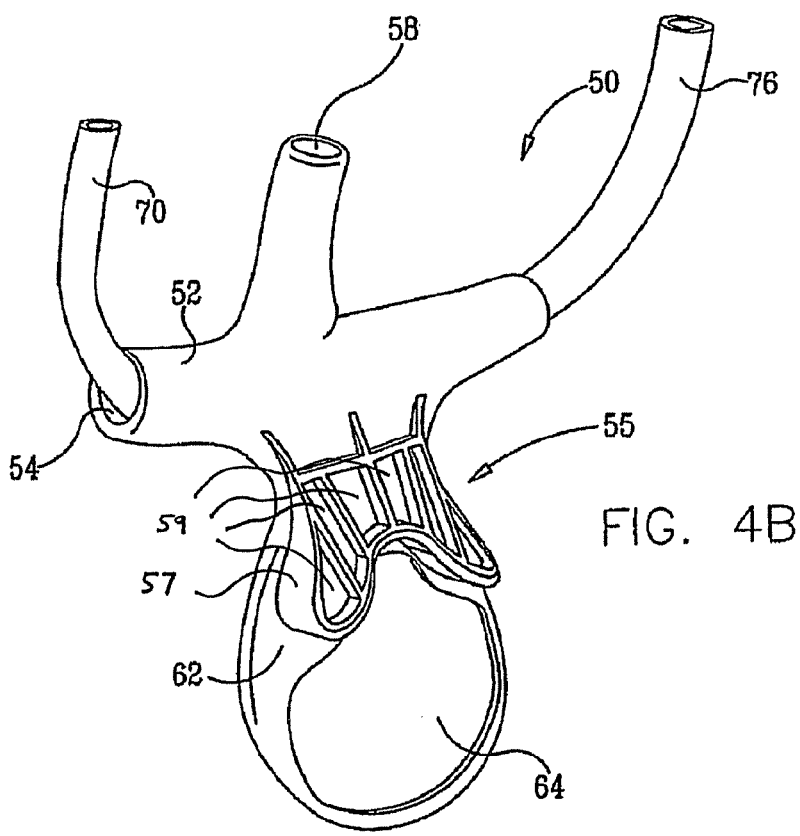
Figure 5A:
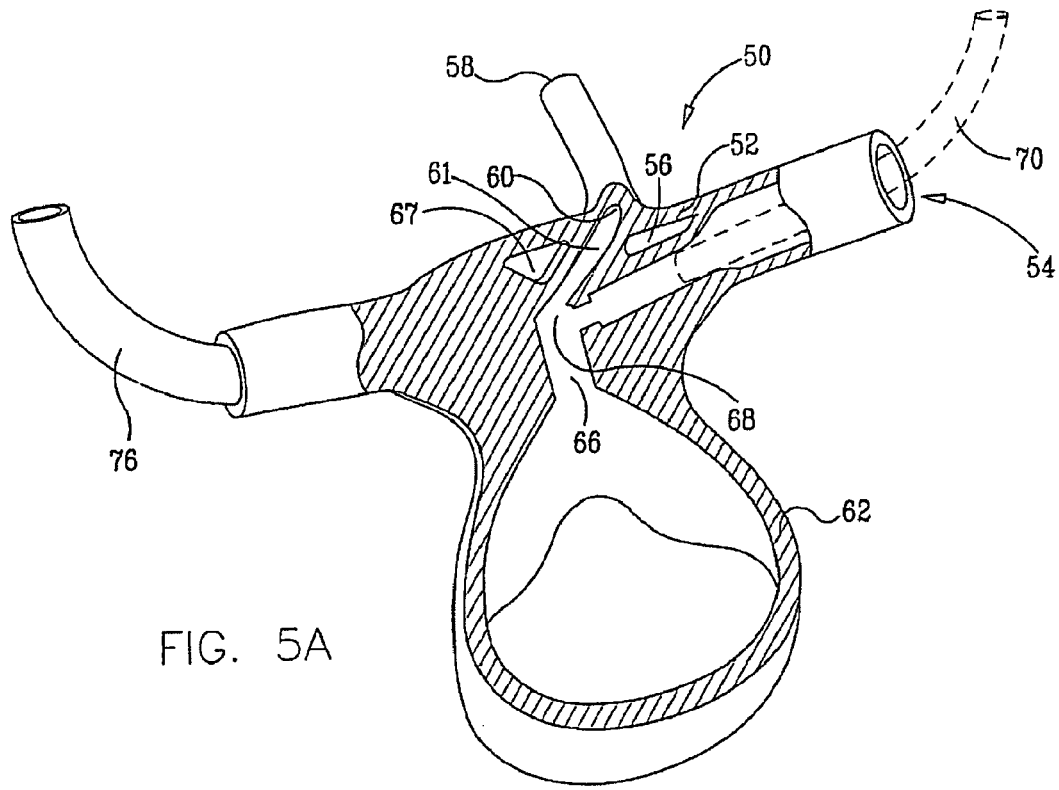
FIGS. 5A, 5B and 5C are partial perspective illustrations with simplified sectional illustrations taken along section lines: VA-VA (in FIG. 5B, the line VA-VA is taken on the whole part), VB-VB (in FIG. 4A), and VC-VC (in FIG. 5B, the line VC-VC is taken on the whole part)
Figure 5B:
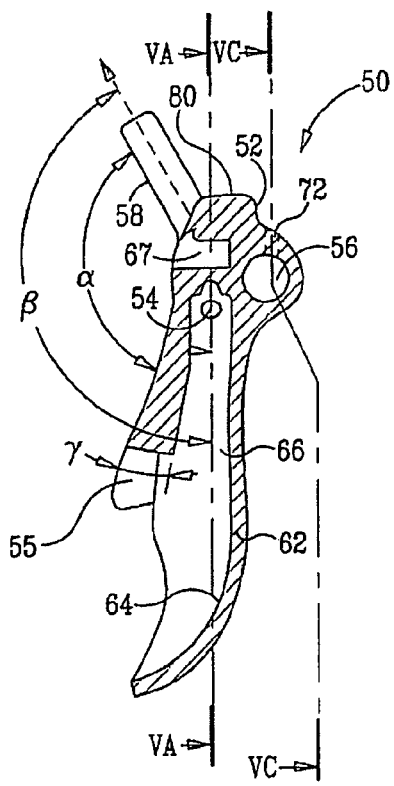
Figure 5C:
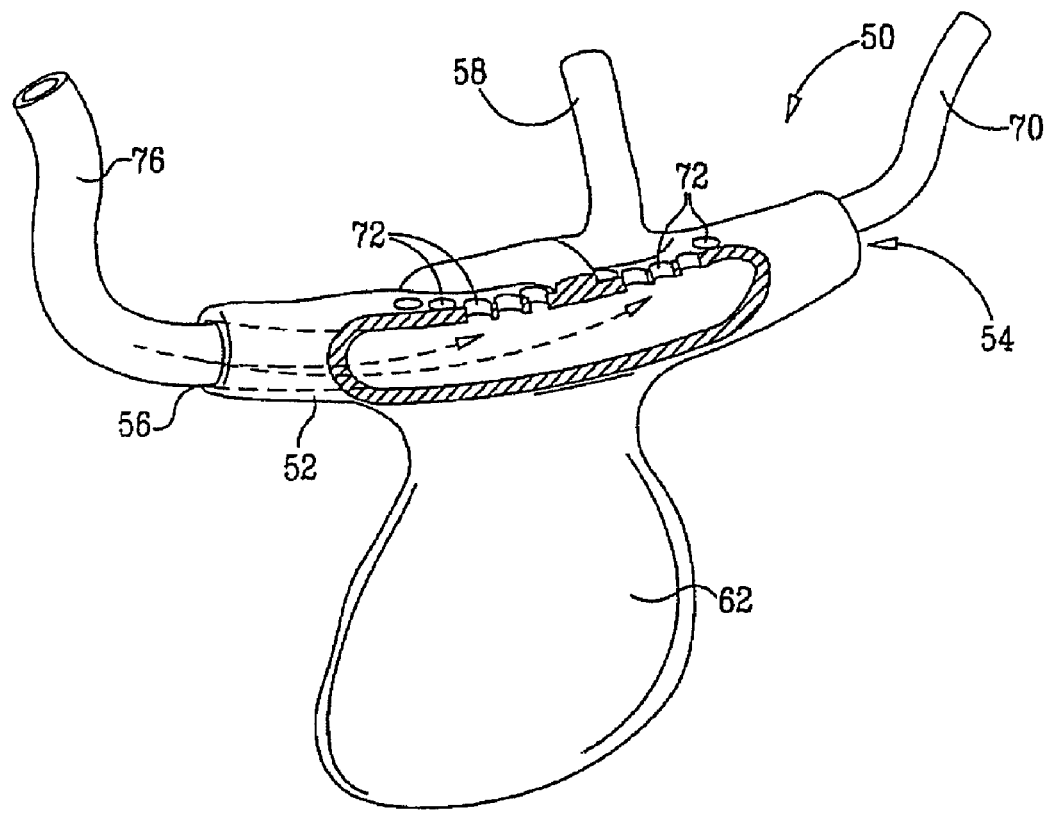

Reference is now made to FIGS. 4A and 4B, which are simplified front-view and rear-view pictorial illustrations of an oral nasal sampling cannula having a single nasal prong, and to FIGS. 5A-5C, which are simplified sectional illustrations thereof.

FIGS. 4A-5C show an oral nasal sampling cannula 50, which is adapted for collection of gases, such as carbon dioxide, exhaled by a subject, and for supplying oxygen to the subject.

The oral nasal sampling cannula 50 comprises a main body portion 52, having formed therein an exhaled breath collection bore 54 and an oxygen delivery bore 56. A hollow nasal prong 58, having an inner end 60 which is in fluid flow communication with a nasal breath collection bore 61, is adapted for at least partial insertion into one nostril of the subject and is integrally formed with the main body portion 52.

An oral scoop element 62, including an internal surface 64, which may be integrally formed with main body portion 52. Oral scoop element 62 terminates at a top portion thereof in an oral breath collection bore 66, which is in fluid flow connection with nasal breath collection bore 61, thereby forming a junction 68. The oral scoop element 62 also includes an internal surface 64, a spacer, formed in the shape of a wedge 65 adapted to maintain a minimum distance between a portion of an oral cavity and a portion of the oral scoop 62. The surface of the wedge 55 may be non-smooth, contoured and/or include structural elements such as rigids, holes, bars, nibs and the like for providing the wedge with additional volume that also adds to its structural rigidity. Another option is forming a wedge as a solid block of material, but this may be undesired in some manufacturing scenarios—for example, when a uniform thickness of material along the cannula system is desired or dictated by the molding process. Wedge 55 may also allow fixed seating against the face (for example, the lip), allow moisture (for example, sweat) evaporation, allow fixed seating against the face for subjects having facial hair, provide comfort and/or avoid sliding (for example, lateral sliding) of the oral nasal sampling cannula 10 on the face of the subject being examined. FIG. 4B shows examples of rigids 57 that may form spaces 59 between them. The oral scoop element 62 may be integrally formed with main body portion 52. The oral scoop element 62 terminates at a top portion thereof in an oral breath collection bore 66, which is in fluid flow connection with nasal breath collection bore 61, thereby forming an essentially single junction 68. The junction can be located above the position shown in FIG. 5A or in any other place that would allow the desired fluid flow. FIG. 5C shows a space extending from the oxygen delivery bore 66, which is in fluid flow communication with an oxygen delivery tube 70 and exits the oral nasal sampling cannula at nasal and possibly oral (not shown) oxygen delivery openings 72, toward the nose and mouth of the subject.

Junction 68 is in fluid flow communication with exhaled breath collection bore 54, which in turn is in fluid flow communication with an exhaled breath collection tube 70, which is adapted to be connected to a suctioning pump, such as that used in a side-stream capnograph (not shown), for example Microcap®, which is commercially available from Oridion of Jerusalem, Israel.

Main body portion 52, may include, optionally at a forward facing surface thereof, or alternatively at any other suitable location, nasal oxygen delivery openings 72 which are in fluid flow communication with oxygen delivery bore 56, as seen with particular clarity in FIG. 5B. Oxygen delivery bore 56, is in fluid flow communication with an oxygen delivery tube 76, which is adapted to be connected to a source of oxygen (not shown).

Oxygen delivery tube 76 and exhaled breath collection tube 70 may optionally be placed around the ears of the subject, thereby stabilizing the oral nasal sampling cannula 50 on the subject's face.

As seen clearly in FIG. 4A, a separator 80 is integrally formed with main body portion 52 at a forward facing surface thereof. Separator 80 is adapted to engage the nose of the subject, thereby distancing the nose from nasal oxygen delivery openings 72 and ensuring that a sufficient oxygen supply reaches the subject's nose, while not closing off the subject's nasal opening, which would incur a resistance to air flow during exhalation.

FIG. 5B, which is a sectional illustration taken along section line VB-VB in FIG. 4A clearly shows the wedge 55, which is structured maintain a minimum distance between the subject's face (for example, the upper lip) and a portion of the oral scoop 62. Also shown in FIG. 5B a hole 67 which may function as a structural element.

Optionally, the oral nasal sampling cannula 50 is suited to the structure of a human face by having an angle, indicated by the letter a in FIG. 5B, between the nasal prong 58 and oral scoop element 62. The cannula may be structured with an angle between the axis of revolution of the interior part of the oral breath collection bore 66 and the axis of revolution of the interior part the nasal prong 58 (this angle is indicated by the letter 13). The cannula structured with a certain angle $\beta$ may allow a desirable flow of the fluid being sampled. Angle $\beta$ may also be defined as the angle between the diameter line of the nasal prong 58 with the center of the oral breath collection bore 66 at line VA intersect with line VB.

Figure 6A:
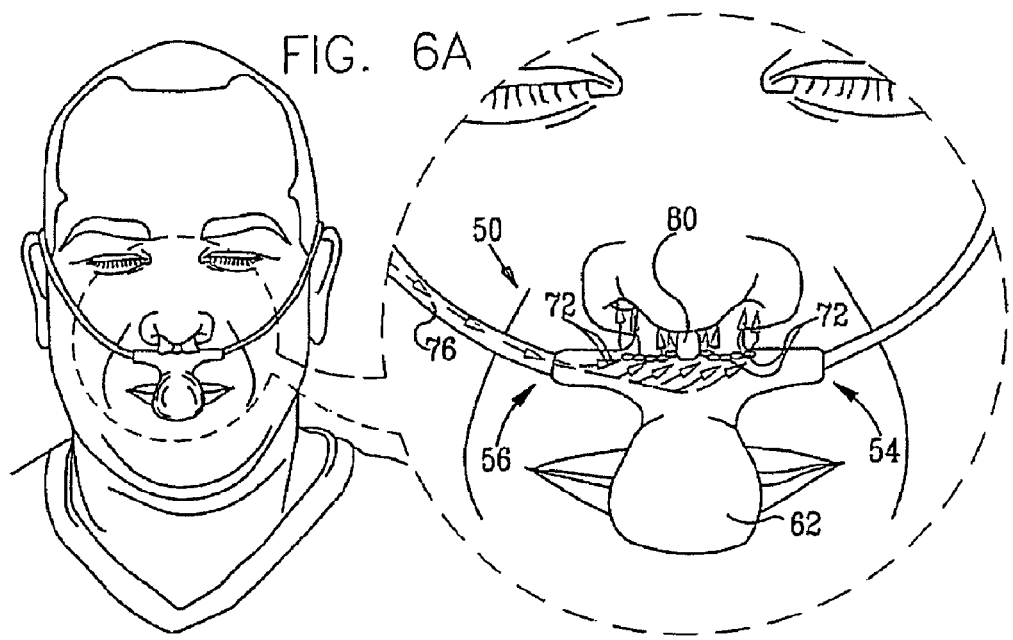
Figure 6B:
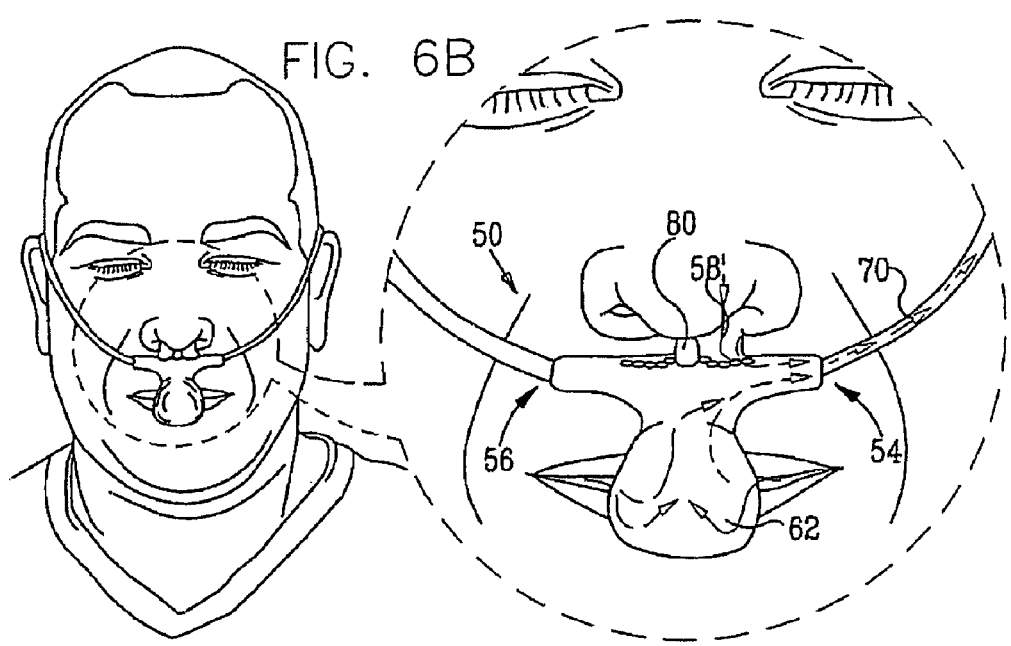
Figure 6C:
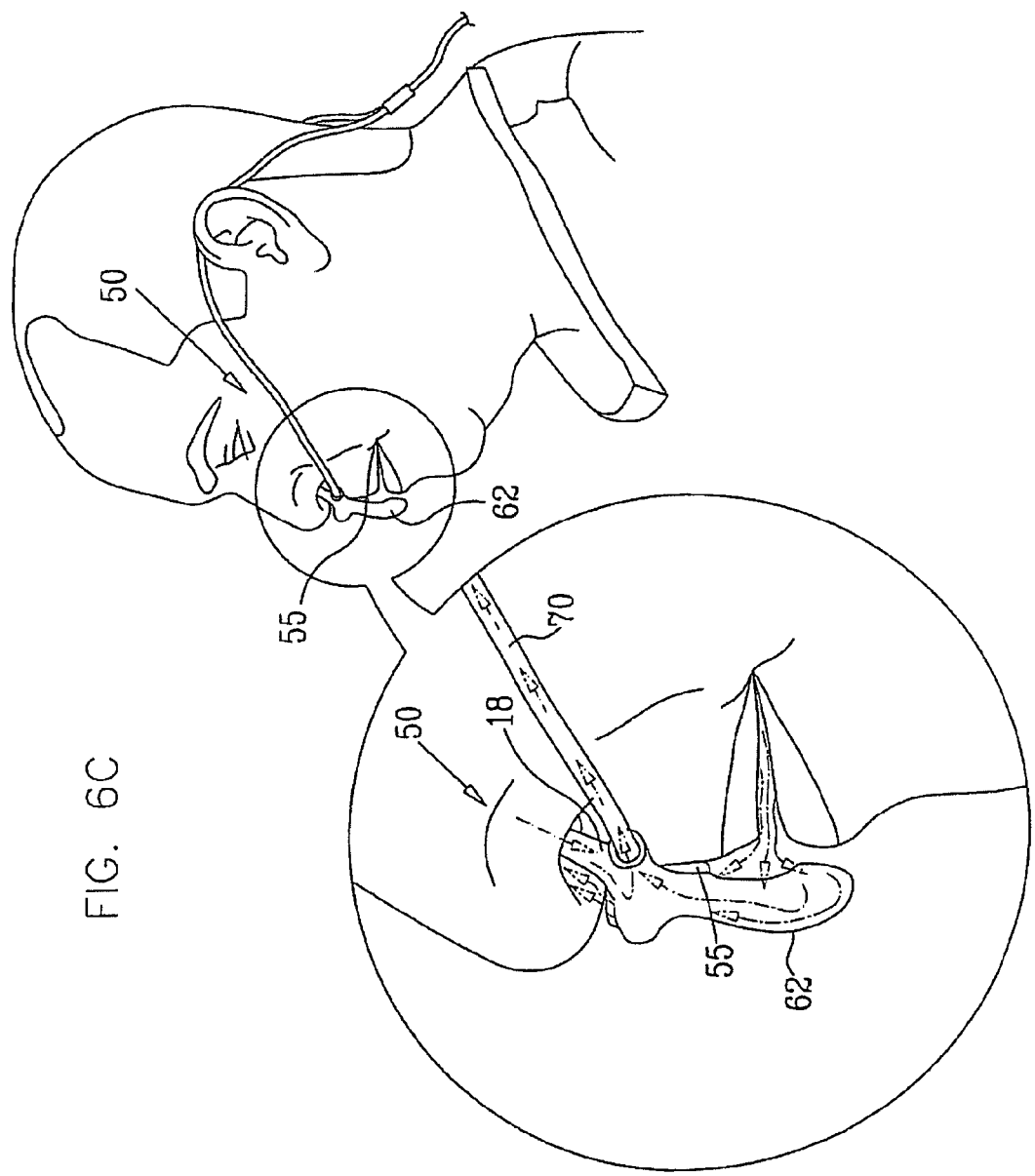

Reference is now made to FIGS. 6A, 6B and 6C, which are schematic illustrations of gas flow in the oral nasal sampling cannula of FIGS. 4A-5C, wherein FIG. 6A depicts oxygen flow and FIGS. 6B and 6C depict sampling of exhaled breath.

As seen in FIG. 6A, oxygen from an oxygen source (not shown) flows through oxygen delivery tube 76, through oxygen delivery bore 56 (FIG. 5B) and exits the oral nasal sampling cannula 50 at nasal oxygen delivery openings 72, toward the nose of the subject.

Turning to FIG. 6B, it is seen that breath exhaled through the subject's nose is directed through nasal prong 58 and nasal breath collection bore 61 (FIG. 5A) toward exhaled breath collection bore 54 (FIG. 5A). In a similar manner, breath exhaled through the subject's mouth is collected in oral scoop element 62, and is directed through oral breath collection bore 66 (FIG. 5B) to exhaled breath collection bore 54. All the exhaled breath collected in exhaled breath collection bore 54 flows into exhaled breath collection tube 70, typically by means of negative pressure supplied by a pumping element (not shown) which may be connected to exhaled breath collection tube 70.

FIG. 6C shows the aerodynamic nature of internal surface 64 (FIG. 4B) of oral scoop element 62. As seen in FIG. 6C, breath exhaled from the subject's mouth hits different points on the internal surface 64 of oral scoop element 62. The multiple different flow surfaces of internal surface 64 ensure that all the exhaled breath that reaches internal surface 64 will be directed toward oral breath collection bore 66 (FIG. 5B). Also shown in FIG. 6C is the wedge 55 that allows increasing the gap between the oral scoop element 62 and the subject's mouth and thus prevents the suction of the oral scoop element 62 into the subject's mouth.

It is appreciated that the importance of the use of several nasal oxygen delivery openings 72 is that during exhalation, which is the period at which the subject's exhaled breath is sampled, it is crucial that the sampled breath is substantially not diluted by the oxygen that is being delivered. In the oral nasal sampling cannula 50, the positive pressure caused by the exhalation is used to push away at least most of the oxygen from the direction of the nostril, thereby ensuring that the majority of the oxygen is not sucked into the nasal prongs 58 and does not dilute the sampled breath. The use of several nasal oxygen delivery openings 72 spreads out the pressure of the oxygen flow, and thus the exhaled air is at an even larger positive pressure relative to the pressure of the oxygen exiting each delivery opening 72, thus more effectively pushing away the oxygen.

It is appreciated that the importance of the use of an oral scoop element is in the fact that a larger percentage of the orally exhaled breath is collected and eventually reaches the sample analysis element. This feature is especially important when monitoring the breath of heavily sedated subjects, which tend to breathe through an open mouth and to have a very low breath rate, typically fewer than 10 breaths per minute, as opposed to greater than 12 breaths per minute in a non-sedated subject.

Additionally, the collection of all the exhaled breath from oral scoop element 62 into the oral breath collection bore 66, which is substantially narrower than oral scoop element 62, amplifies the pressure of the orally exhaled breath, which is typically very low, specifically in sedated subjects.

Moreover, amplification of the pressure of orally exhaled breath is important for the accuracy of the sampling due to the fact that the pressure created during exhalation at the exit of a mouth which is wide open is much lower than the pressure created by the flow of exhaled breath via the nostril.

It is also appreciated that the sampled exhaled breath is substantially not diluted by ambient air due to pressure gradients within the system, and a majority of the sampled exhaled breath does not escape from the system.

If the subject is performing oral and nasal breathing, there is a slightly higher pressure in nasal breath collection bore 61 (FIG. 5A) and in oral breath collection bore 66 (FIG. 5B), and a slightly more negative pressure in exhaled breath collection bore 54 (FIG. 5A) due to the suctioning pump which is connected to exhaled breath collection tube 70, thereby ensuring that the exhaled breath is removed from the oral nasal sampling cannula 50 and is optionally transported towards a capnograph. Due to positive pressure within the oral scoop element, essentially no ambient air enters breath collection bores 61 and 66 and the exhaled breath is essentially not diluted.

In the case of nasal breath only, the air in oral scoop element 62 is of the same pressure as the air all around it, whereas there is slightly higher pressure in the nasal breath collection bore 61 pushing down via the junction 68 (FIG. 5A), to create a relatively positive pressure at the oral breath collection bore 66, thereby ensuring that essentially no ambient air will enter the system. Additionally, essentially most of the exhaled breath does not escape the system due to the pumping element that constantly creates a relatively low pressure in exhaled breath collection bore, thereby ensuring that essentially a sufficient amount of the exhaled breath will travel toward the exhaled breath collection tube 70 and not out toward the ambient air.

In a similar manner, in the case of oral breath only, the air in nasal prong 58 and in nasal breath collection bore 61 is of the same pressure as the air all around it, whereas there is a slightly higher pressure in the oral breath collection bore 66 pushing up via the junction 68, to create a relatively positive pressure at the nasal breath collection bore 61, thereby ensuring that essentially no ambient air will enter the system. Additionally, essentially a majority of the exhaled breath does not escape the system due to the pumping element that constantly creates a relatively negative pressure in exhaled breath collection bore, thereby ensuring that essentially a sufficient amount of the exhaled breath will travel toward the exhaled breath collection tube 70 and not out toward the ambient air.

Figure 7A:
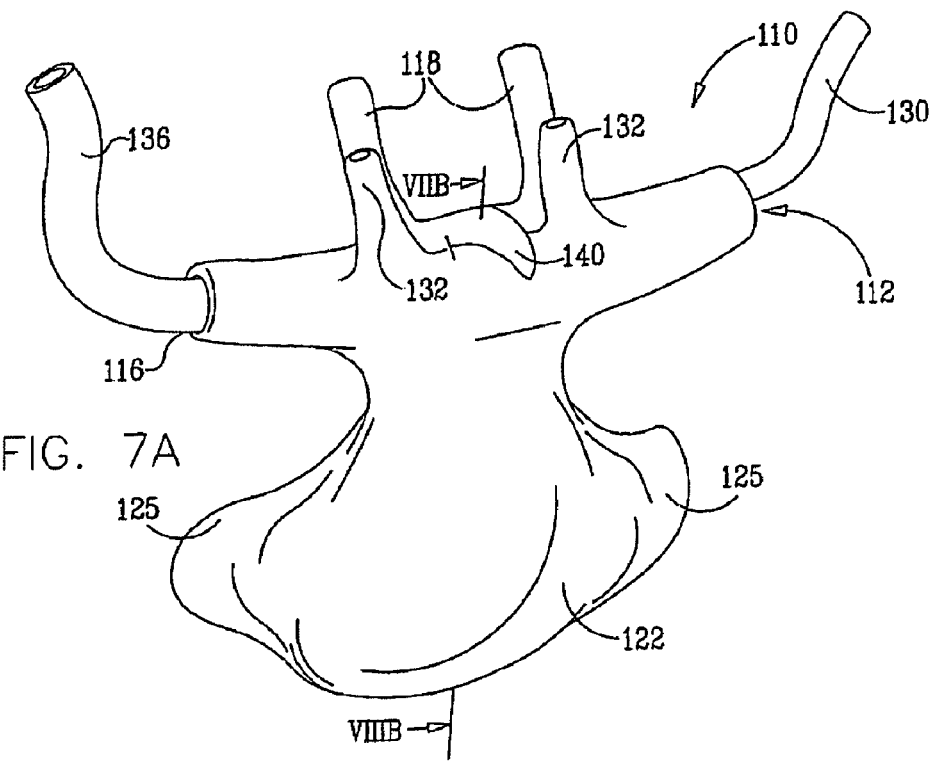
FIGS. 7A and 7B are simplified front-view and rear-view pictorial illustrations of an oral nasal sampling cannula having an enlarged oral scoop.
Figure 7B:
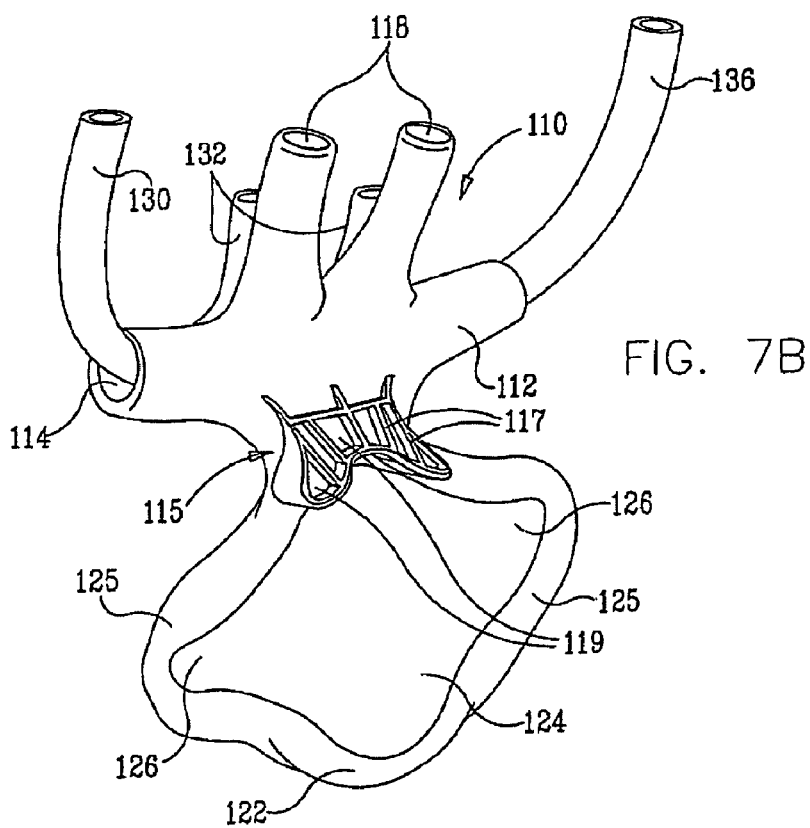
Figure 8A:
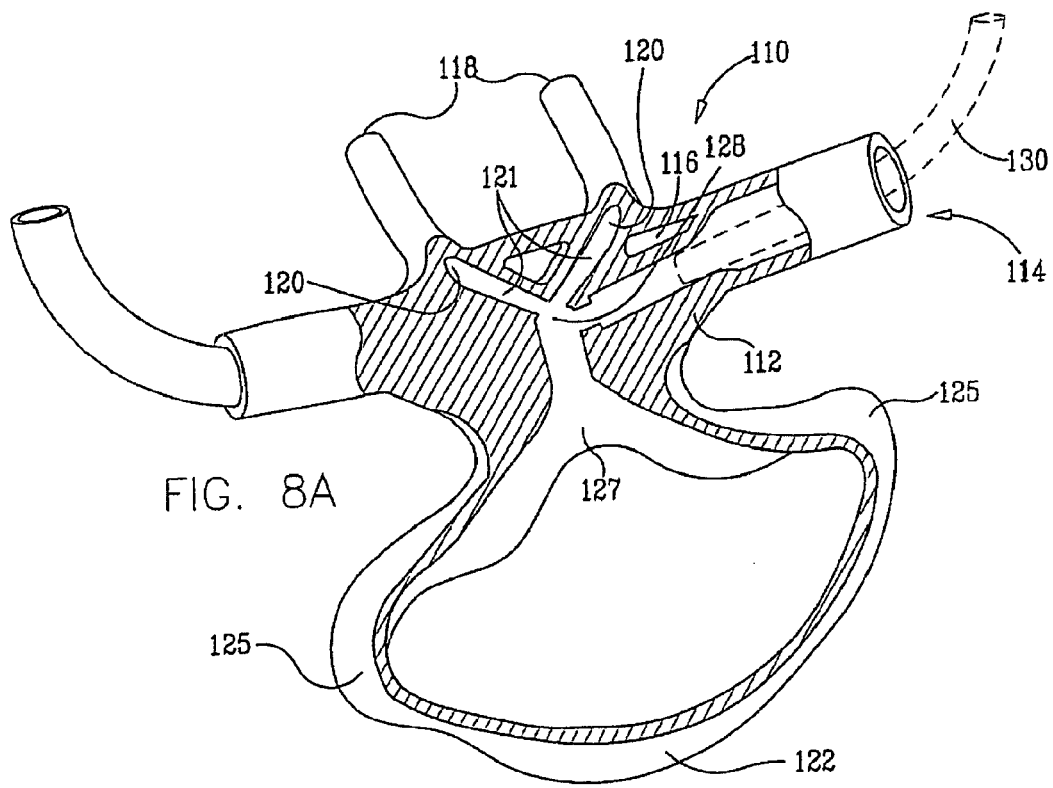
FIGS. 8A, 8B and 8C are partial perspective illustrations with simplified sectional illustrations taken along section lines: VIIIA-VIIIA (in FIG. 8B, the line VIIIA-VIIIA is taken on the whole part), VIIIB-VIIIB (in FIG. 7A) and VIIIC-VIIIC (in FIG. 8B, the line VIIIC-VIIIC is taken on the whole part)
Figure 8B:
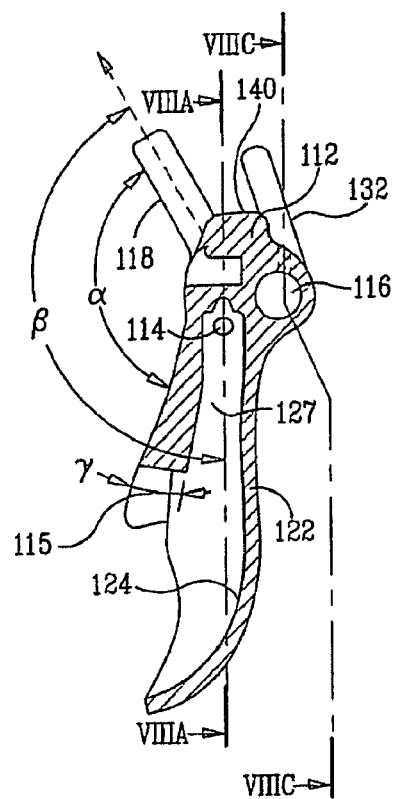

Reference is now made to FIGS. 7A and 7B, which are simplified front-view and rear-view pictorial illustrations of an oral nasal sampling cannula having an enlarged oral scoop, which is constructed and operative in accordance with an embodiment and to FIGS. 8A and 8B, which are simplified sectional illustrations thereof.

FIGS. 7A-8C show an oral nasal sampling cannula 110, which is adapted for collection of gases, such as carbon dioxide, exhaled by a subject, and for supplying oxygen to the subject.

The oral nasal sampling cannula 110 comprises a main body portion 112, having formed therein an exhaled breath collection bore 114 and an oxygen delivery bore 116. A pair of hollow nasal prongs 118, having inner ends 120, which are in fluid flow communication with a pair of nasal breath collection bores 121, is adapted for at least partial insertion into the nostrils of the subject and is integrally formed with the main body portion 112.

Figure 8C:
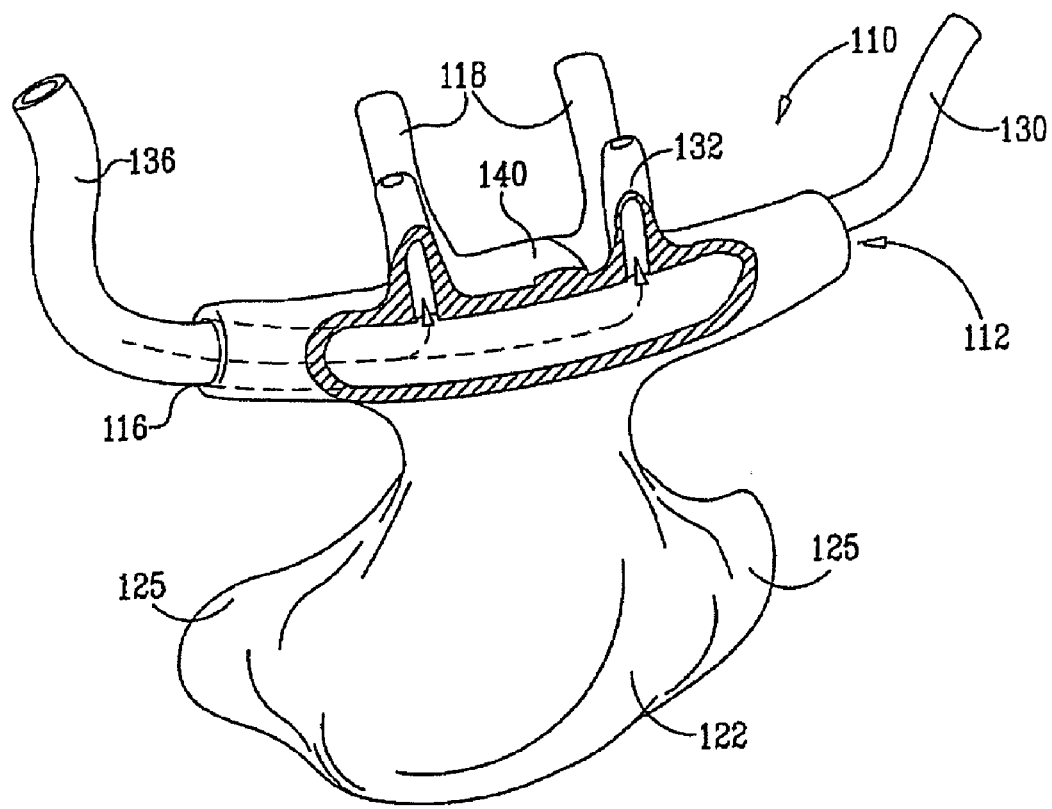

An oral scoop element 122, including an internal surface 124, is integrally formed with main body portion 112. Oral scoop element 122 additionally has formed thereon a pair of extension portions 125, each having an internal surface 126, and terminates at a top portion thereof in an oral breath collection bore 127. Oral breath collection bore 127 is in fluid flow connection with nasal breath collection bores 121, thereby forming a single junction 128. The oral scoop element 122 also includes an internal surface 124, a spacer, formed in the shape of a wedge 115 adapted to maintain a minimum distance between a portion of an oral cavity and a portion of the oral scoop 122. The surface of the wedge 115 may be non-smooth, contoured and/or include structural elements such as rigids, holes, bars, nibs and the like, to form additional structural rigidity, to allow fixed seating against the face (for example, the lip), to allow moisture (for example, sweat) evaporation, to allow fixed seating against the face for subjects having facial hair, to provide comfort and/or to avoid sliding (for example, lateral sliding) of the oral nasal sampling cannula 10 on the face of the subject being examined. FIG. 7B shows examples of rigids 117 that may form spaces 119 between them. The oral scoop element 122 may be integrally formed with main body portion 112. The oral scoop element 122 terminates at a top portion thereof in an oral breath collection bore 127, which is in fluid flow connection with nasal breath collection bores 121, thereby forming an essentially single junction 128. The junction can be located above the position shown in FIG. 8A or in any other place that would allow the desired fluid flow. FIG. 8C shows the spacer 113 extending from the oxygen delivery bore 127, which is in fluid flow communication with an oxygen delivery tube 130 and exits the oral nasal sampling cannula 110 at nasal oxygen delivery prongs 132, toward the nose of the subject.

Single junction 128 is in fluid flow communication with exhaled breath collection bore 114, which in turn is in fluid flow communication with an exhaled breath collection tube 130, which is adapted to be connected to a suctioning pump, such as that used in a side-stream capnograph (not shown), for example Microcap®, which is commercially available from Oridion of Jerusalem, Israel.

Main body portion 112 includes, optionally at a forward facing surface thereof or alternatively at any other suitable location, nasal oxygen delivery prongs 132 which are typically shorter than nasal prongs 118 such that they do not enter the subject's nostrils. The exits of the nasal oxygen delivery prongs 132 facing the nostrils may have different shapes, for example a funnel shape. The nasal oxygen delivery prongs 132 are in fluid flow communication with oxygen delivery bore 116, as seen with particular clarity in FIG. 8B. Oxygen delivery bore 116 is in fluid flow communication with an oxygen delivery tube 136, which is adapted to be connected to a source of oxygen (not shown).

Oxygen delivery tube 136 and exhaled breath collection tube 130 may optionally be placed around the ears of the subject, thereby stabilizing the oral nasal sampling cannula 110 on the subject's face.

As seen clearly in FIG. 7A, a separator 140 is integrally formed with main body portion 112 at a forward facing surface thereof. Separator 140 is adapted to engage the nose of the subject, thereby distancing the nostrils from nasal oxygen delivery prongs 132 and ensuring that a sufficient oxygen supply reaches the subject's nose, while not closing off the subject's nasal opening, which would incur a resistance to air flow during exhalation.

FIG. 8B, which is a sectional illustration taken along section line VIIB-VIIB in FIG. 7A clearly shows the wedge 115, which is structured maintain a minimum distance between the subject's face (for example, the upper lip) and a portion of the oral scoop 122. Also shown in FIG. 5B a hole 117 which may function as a structural element.

Optionally, the oral nasal sampling cannula 110 is suited to the structure of a human face by having an angle, indicated by the letter $\alpha$ in FIG. 8B, between the at least one nasal prong 118 and oral scoop element 122. The cannula may be structured with an angle between the axis of revolution of the interior part of the oral breath collection bore 127 and the axis of revolution of the interior part of at least one of the nasal prong 118 (this angle is indicated by the letter $\beta$). The cannula structured with a certain angle $\beta$ may allow a desirable flow of the fluid being sampled. Angle $\beta$ may also be defined as the angle between the diameter line of the nasal prong 118 with the center of the oral breath collection bore 127 at line VIIA intersect with line VIIB.

Figure 9A:
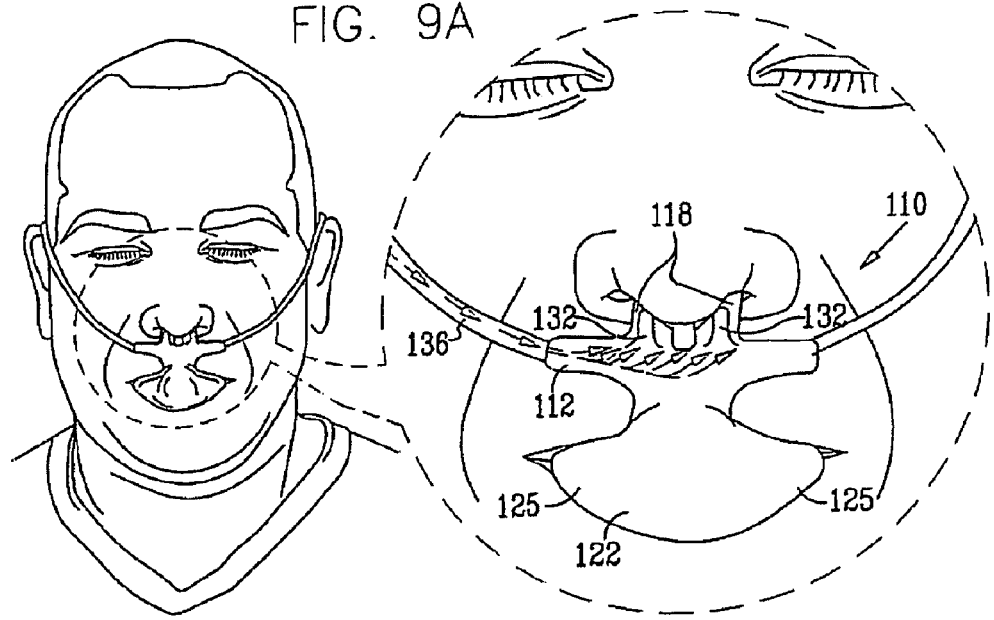
Figure 9B:
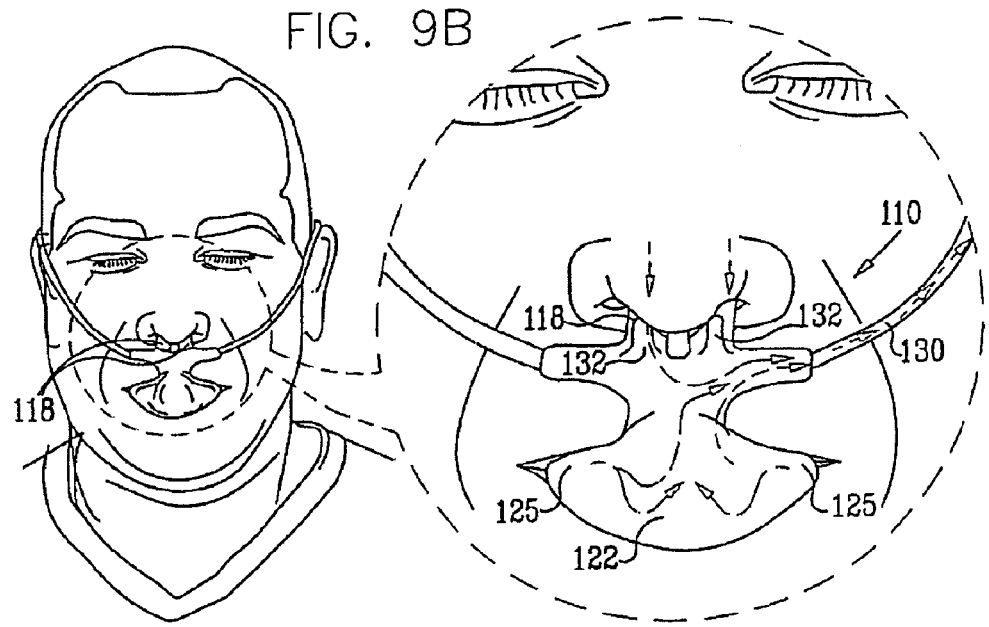

Reference is now made to FIGS. 9A, 9B and 9C, which are schematic illustrations of gas flow in the oral nasal sampling cannula 110 of FIGS. 7A-8C, wherein FIG. 9A depicts oxygen flow and FIGS. 9B and 9C depict sampling of exhaled breath.

As seen in FIG. 9A, oxygen from an oxygen source (not shown) flows through oxygen delivery tube 136, through oxygen delivery bore 116 (FIG. 8B) and exits the oral nasal sampling cannula 110 at nasal oxygen delivery prongs 132, toward the nose of the subject.

Turning to FIG. 9B, it is seen that breath exhaled through the subject's nose is directed through nasal prongs 118 and nasal breath collection bores 121 (FIG. 8A) toward exhaled breath collection bore 114 (FIG. 8A). In a similar manner, breath exhaled through the subject's mouth is collected by oral scoop element 122 and by extension portions 125, and is directed through oral breath collection bore 127 (FIG. 8B) to exhaled breath collection bore 114. All of the exhaled breath collected in exhaled breath collection bore 114 flows into exhaled breath collection tube 130, typically by means of negative pressure supplied by a pumping element (not shown) which may be connected to exhaled breath collection tube 130.

FIG. 9C shows the aerodynamic nature of internal surfaces 124 and 126 (FIG. 7B) of oral scoop element 122 and extension portions 125 thereof. As seen in FIG. 9C, breath exhaled from the subject's mouth hits different points on the internal surfaces 124 and 126 of oral scoop element 122 and extension portions 125 thereof. The multiple different flow surfaces of internal surfaces 124 and 126 ensure that all the exhaled breath that reaches internal surfaces 124 and 126 will be directed toward oral breath collection bore 127 (FIG. 8B).

It is appreciated that the nasal oxygen delivery prongs 132 are shorter than the nasal prongs 118 such that during exhalation, which is the period at which the subject's exhaled breath is sampled, it is crucial that the sampled breath is substantially not diluted by the oxygen that is being delivered. In the oral nasal sampling cannula 110, the positive pressure caused by the exhalation is used to push away at least a majority of the oxygen from the direction of the nostril, thereby ensuring that most of the delivered oxygen is not sucked into the nasal prongs 118 and essentially does not dilute the sampled breath. If the nasal oxygen delivery prongs 132 were at the same height as the nasal prongs 118, even if the oxygen were pushed back and away during exhalation, some oxygen would still enter the sampling nasal prongs 118 thereby diluting the sample. The fact that the nasal oxygen delivery prongs 132 are lower than sampling nasal prongs 118 prevents this from occurring.

It is appreciated that the importance of the use of an oral scoop element is in the fact that a larger percentage of the orally exhaled breath is collected and eventually reaches the sample analysis element. The use of extension portions 125 ensures that generally an oral breath collection device covers a majority of the subject's mouth, thereby collecting most of the subject's orally exhaled breath. These features are especially important when monitoring the breath of heavily sedated subjects, which tend to breathe through an open mouth and to have a very low breath rate, typically fewer than 10 breaths per minute, as opposed to greater than 12 breaths per minute in a non-sedated subject.

Additionally, the collection of most of the exhaled breath from oral scoop element 122 and extension portions 125 into the oral breath collection bore 127, which is substantially narrower than oral scoop element 122 and extension portions 125 thereof, amplifies the pressure of the orally exhaled breath, which is typically very low, specifically in sedated subjects.

Moreover, amplification of the pressure of orally exhaled breath is important for the accuracy of the sampling due to the fact that the pressure created during exhalation at the exit of a mouth which is wide open is much lower than the pressure created by the flow of exhaled breath via the nostrils.

It is also appreciated that the sampled exhaled breath is substantially not diluted by ambient air due to pressure gradients within the system, and a majority of the sampled exhaled breath does not escape from the system.

If the subject is performing oral and nasal breathing, there is slightly higher pressure in nasal breath collection bores 121 (FIG. 8A) and in oral breath collection bore 127 (FIG. 8B), and slightly more negative pressure in exhaled breath collection bore 114 (FIG. 8A) due to the suctioning pump which is connected to exhaled breath collection tube 130, thereby ensuring that at least most of the exhaled breath is removed from the oral nasal sampling cannula 110 and is optionally transported towards a gas analyzer such as a capnograph. Due to the relatively positive pressure within the oral scoop element 122, essentially no ambient air enters breath collection bores 121 and 127 and the exhaled breath is substantially not diluted.

In the case of nasal breath only, the air in oral scoop element 122 and in extension portions 125 is of the same pressure as the air all around it, whereas there is slightly higher pressure in the nasal breath collection bores 121, thereby ensuring that essentially no ambient air will enter the oral nasal sampling cannula 110. Additionally, essentially a majority of the exhaled breath does not escape the system due to the pumping element that constantly creates a relatively negative pressure in exhaled breath collection bore, thereby ensuring that most of the exhaled breath will travel toward the exhaled breath collection tube 130 and not out toward the ambient air.

In a similar manner, in the case of oral breath only, the air in nasal prongs 118 and in nasal breath collection bores 121 is of the same pressure as the air all around it, whereas there is slightly higher pressure in the oral breath collection bore 127 pushing up via the single junction 128, to create a relatively positive pressure at the nasal breath collection bores 121, thereby ensuring that essentially no ambient air will enter the oral nasal sampling cannula 110. Additionally, essentially a majority of the exhaled breath does not escape the system due to the pumping element that constantly creates a relatively negative pressure in exhaled breath collection bore, thereby ensuring that most of the exhaled breath will travel toward the exhaled breath collection tube 130 and not out toward the ambient air.

A Breath Flow Measurement Sub-System Implemented Into the Oral-Nasal Cannula System of the '247 Publication An oral-nasal cannula system, according to an embodiment, may include a carbon dioxide ($CO_2$) sampling sub-system based on the system of the '247 publication, and a breath flow measurement sub-system—wherein the $CO_2$ sampling sub-system and the breath flow measurement sub-system are adapted to operate independently, essentially without cross-interference.

Initially, it should be noted that while $CO_2$ sampling involves actual traveling of the sampled gasses to a capnograph by virtue of a pump at the capnograph's end, breath flow measurement is based on measuring pressure waves that propagate through the gasses without actual movement of gas molecules from the collection area to the pressure meter. Therefore, the term "sampling" is used here in regard to $CO_2$, while the term "measurement" is used in connection with breath flow.

Advantageously, in an embodiment, the breath flow measurement sub-system is not added to the $CO_2$ sampling sub-system merely as a piggyback solution. Such a piggyback solution, that may include, for example, two cannula systems (one for $CO_2$ and one for flow) glued together or otherwise attached, may be cumbersome and annoying for the patient, since duplicate nasal and oral inlets would be competing for space in or near his nostrils and in front of his mouth. In addition, twice as many elongated tubes would be extending from the patient to the metering devices, causing additional disorder.

Even more advantageously, the breath flow measurement sub-system is not combined with the $CO_2$ sampling sub-system merely by way of simple splitting of a single patient-side cannula system (such as oral nasal sampling cannula 10 of FIGS. 1A-2C or a similar oral nasal sampling cannula adapted for flow measurement) into two lines only in proximity to the metering devices. Such a simple splitting solution may lead to inaccurate $CO_2$ and/or breath flow readings at the devices. That is, if exhaled breath is commonly collected without any separation at the patient-side cannula system area, then the pump, which is used in a side-stream capnograph (as often necessary with non-intubated patients), may cause pressure fluctuations that disrupt the breath flow measurement. In addition, partial blockages that may occur in the common tube due to various secretions, may also cause sudden pressure changes that influence the breath flow measurement.

In such a simple splitting solution, errors may even arise already at the patient-side cannula system. For example, if nasal collection is common to both $CO_2$ and flow (such as when using oral nasal sampling cannula 10 of FIGS. 1A-2C), then nasal breath may be lost by escaping through the internal Y junction (also referred to as "single junction") 28 (FIG. 2A) and then out via the oral scoop. An internal Y junction configuration, such as Y junction 28, may indeed be necessary for optimal $CO_2$ sampling; however, in this scenario, it may clearly miss the purpose of its existence.

Hence, instead of a simple piggyback solution or a simple splitting solution, the present disclosure suggests an advantageous design for combining the two sub-systems, while preventing, or at least mitigating, cross-interference between the two.

The advantageous design is based, primarily, on an early separation of breath collected for $CO_2$ sampling and for breath flow measurement. Optionally, the early separation is done only with nasal breath (while oral breath is separated a bit later, in proximity to the oral inlet—but not as far as in the simple splitting solution discussed previously), by providing two separate prongs—one for $CO_2$ and one for breath flow measurement. That way, when pressure is created by nasal breathing, this pressure is not lost by escaping out via the oral scoop—which would have occurred if the nasal collection were common to both $CO_2$ and flow. Instead, the nasal pressure is delivered separately in the direction of the flow meter, and not through the internal Y junction 28 (FIG. 2A) which is in fluid contact with the oral scoop.

In contrast to nasal pressure which may escape through the oral scoop if not separated early, oral pressure tends to behave differently. When pressure is created by oral breathing, it does not normally escape via the Y junction 28 and out the nasal prongs—due to the relative narrowness of the nasal prongs that causes the pressure to be channeled towards the $CO_2$ sampling exit. Therefore, early separation of oral breath may not be necessary for preserving this pressure for flow measurement purposes. Still, such a separation may still be performed if desired, and its existence may not degrade performance.

The oral-nasal cannula system may further include an oxygen delivery sub-system. The oral-nasal cannula system may further include a capnograph connected to said $CO_2$ sampling sub-system, and a flow meter connected to said breath flow measurement sub-system.

Figure 10:
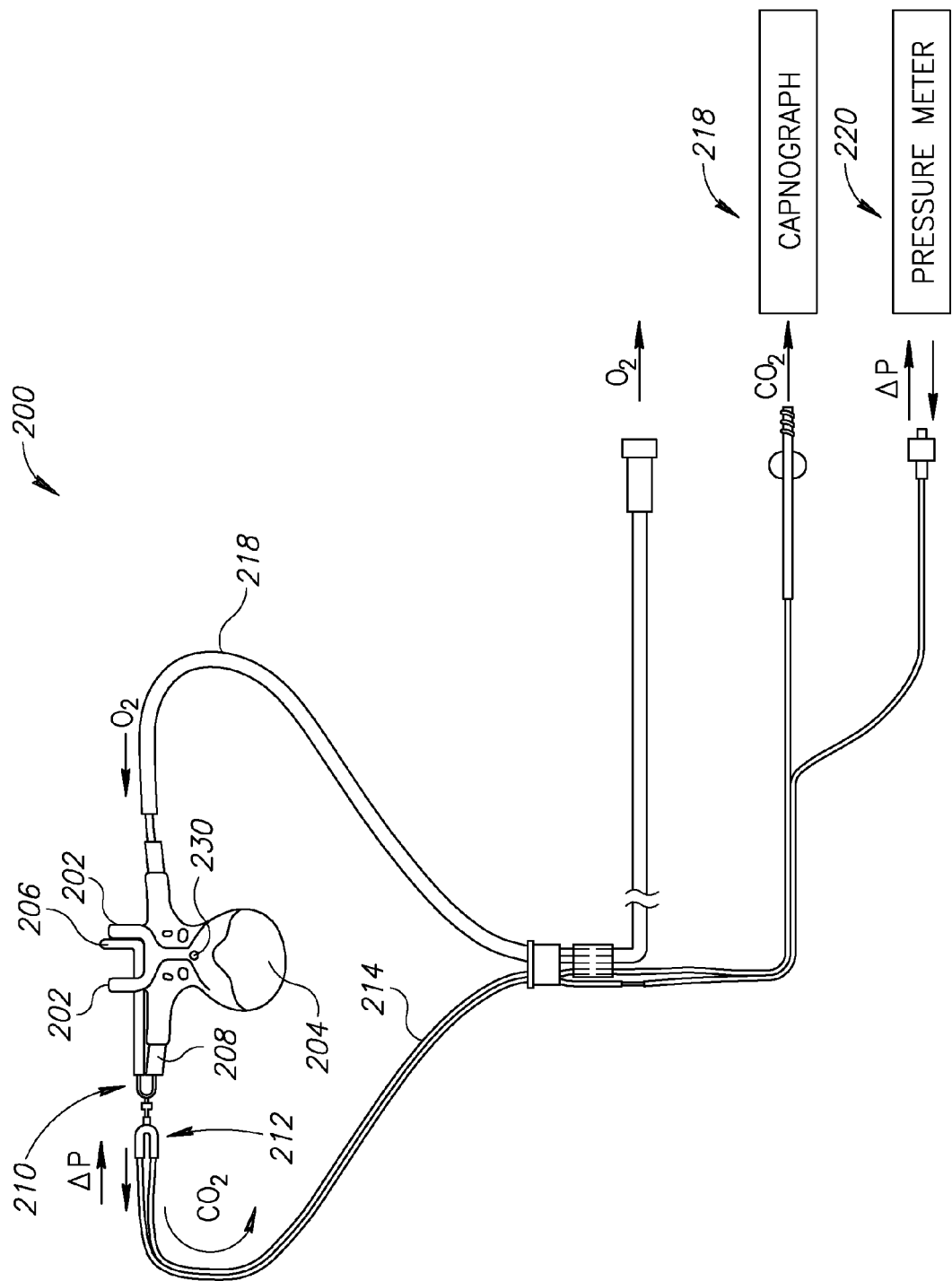
FIG. 10 shows an oral-nasal cannula system having both a $CO_2$ sampling sub-system and a breath flow measurement sub-system.
Figure 11:
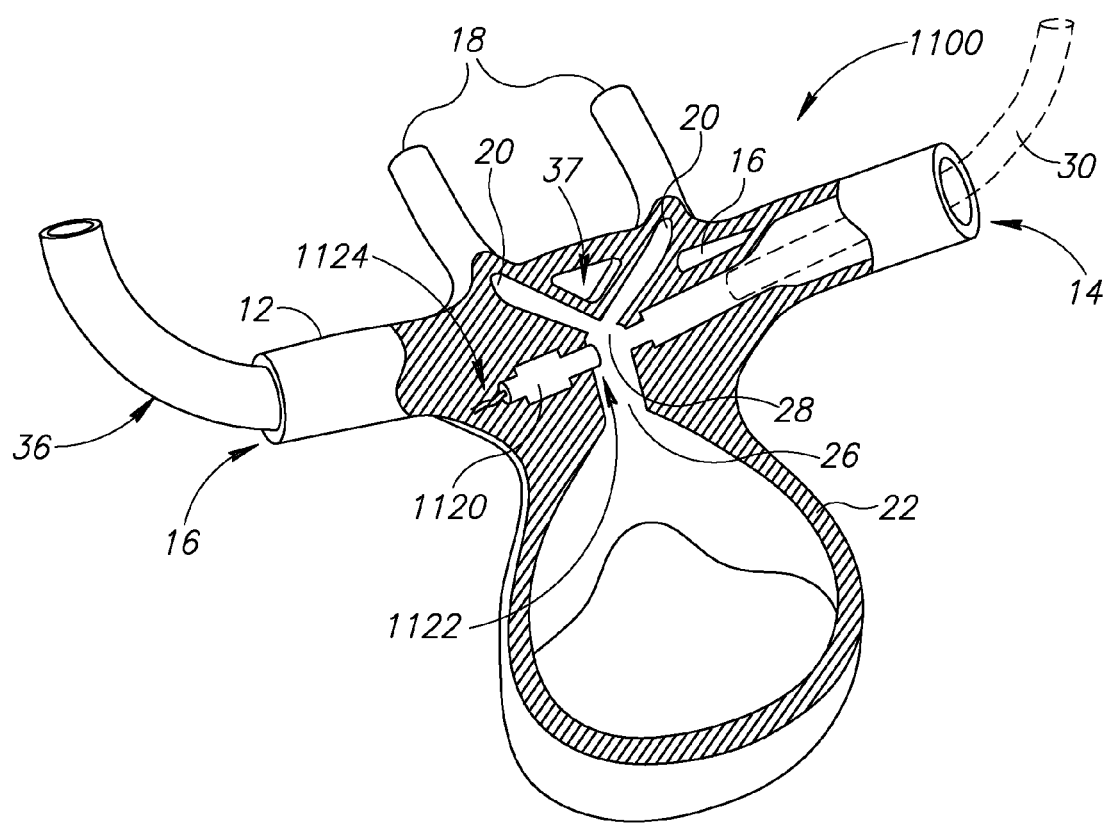
FIG. 11 is a pictorial illustration of an oral nasal cannula having a self-contained pressure sensor.

Reference is now made to FIG. 10, which shows an oral-nasal cannula system 200 having both a $CO_2$ sampling sub-system and a breath flow measurement sub-system. The $CO_2$ sampling sub-system is comprised of at least one nasal $CO_2$ sampling prong, for example—two nasal $CO_2$ sampling prongs 202. The $CO_2$ sampling sub-system is additionally comprised of an oral $CO_2$ sampling scoop 204.

The nasal $CO_2$ sampling prongs 202 and the oral $CO_2$ sampling scoop 204 may intersect internally (not shown) at a junction from which a $CO_2$ sampling line originates, such as breath collection bore 14 (FIGS. 1A-3C).

The breath flow measurement sub-system may use oral $CO_2$ sampling scoop 204 as its oral breath flow measurement means. Scoop 204, given its relatively large area and coverage, may be adapted to collect oral breath, which often gets dispersed over a large area due to the open mouth. In an alternative embodiment (not shown), a different means of collecting oral breath for $CO_2$ sampling may be used, such as a prong, a scoop smaller than scoop 204, and/or the like. For example, an oral flow prong may be positioned essentially within an existing scoop, towards the upper part of the scoop and next to its drainage area (shown at 230 in FIG. 10), so that the scoop collects oral breath for both $CO_2$ sampling and flow measurement, but the two features are separated towards the scoops drainage area.

The breath flow measurement sub-system may additionally comprise of at least one nasal breath flow measurement prong 206, which is adapted to receive exhaled nasal breath separate from nasal $CO_2$ sampling prongs 202.

In an embodiment (not shown), a nasal breath flow measurement means may be part of a nasal $CO_2$ sampling prong or prongs, in such a way that exhaled nasal breath is still physically separated, for example by a divider within the $CO_2$ sampling prong(s), between exhaled breath that is used for $CO_2$ sampling and exhaled breath that is used for breath flow measurement.

In an embodiment (not shown), an oral breath flow measurement means may be separate from an oral $CO_2$ sampling means (shown in FIG. 10 as scoop 204). For example, a scoop may be physically divided such that it provides separate lines for $CO_2$ sampling and breath flow measurement. Alternatively, a physical division may be present farther away from the scoop itself, for example at a top drainage area 230 of the scoop where it narrows down. There, where the collected breath exits the scoop, a physical division of the exit port may exist, separating $CO_2$ sampling and breath flow measurement.

Breath flow measurement prong 206 may be connected to a line 208 (which is, in turn, connected to prongs 202 and scoop 204) using a joiner 210, adapted to join gas flow from breath flow measurement prong 206, prongs 202 and scoop 204. Then, a splitter 212 splits the gas flow into two separate tubes, a $CO_2$ sampling tube 214 that may be connected to a capnograph 218, and a breath flow measurement tube 216 that may be connected to a pressure meter 220.

The term "gas flow", as referred to herein in regard to $CO_2$ sampling, relates to actual gas flow, wherein when the term is used in regard to breath flow measurement, it relates to a movable pressure wave that does not necessarily involve actual gas flow. In addition, the breath flow measurement may be focused on both exhalation and inhalation, whereas the $CO_2$ sampling may be focused, naturally, only on exhalation. It should be noted that a capnograph may operate continuously and perform sampling even during inhalation, but will show a reading of zero $CO_2$ sampling during inhalation.

The joining and the splitting of the tubing may ensure that both capnograph 218 and pressure meter 220 receive a similar or an identical gas sample (or a pressure wave, in the case of the breath flow measurement), which represents both nasal and oral breathing (if both exist. Breathing may occasionally include only nasal or only oral breathing.) In addition, the relatively short distance between joiner 210 and splitter 212, may ensure that actual gas movement and/or pressure drop is limited to essentially this section and therefore does not cause substantial reading errors at the capnograph and/or the flow meter. Generally, the joiner and the splitter provide what may be referred to as a "mixture area", which, as mentioned, allows gas arriving from line 208 (which includes gasses from prongs 202 and scoop 204) to mix with gas arriving from breath flow measurement prong 206. This mixture area is further discussed below with reference to FIGS. 12 and 13.

Oral-nasal cannula system 200 optionally includes an oxygen ($O_2$) delivery sub-system, including a tube 222 operative to supply the subject, orally and/or nasally, with oxygen. The oxygen delivery sub-system and its oral and/or nasal delivery features are further shown in FIGS. 1A-9C and described above.

In an embodiment (not shown), in addition to or instead of collecting nasal breath for breath flow measurement using a separate prong such as prong 206, one or more holes in the top area of the oral-nasal cannula system may be used for this purpose. For example, holes such as 32 (FIGS. 1A and 2C), 37 (FIG. 1C), 72 (FIGS. 4A and 4C) or 132 (FIG. 8C) which are facing the patient's nose, may be used for collection of nasal breath for measuring flow—instead of for supplying oxygen. It should be noted that the figures referenced in the previous sentence show only embodiments of a basic oral-nasal cannula system without breath flow measurement. Accordingly, the holes shown in these figures are only referred to here for showing possible locations of holes for the nasal breath flow sampling. Optionally, oxygen delivery tube 36 may be connected to a joiner and a splitter similar to what is shown in FIG. 10, replacing breath flow measurement prong 206 which is connected to joiner 110 and splitter 112 in FIG. 10.

Figure 12:
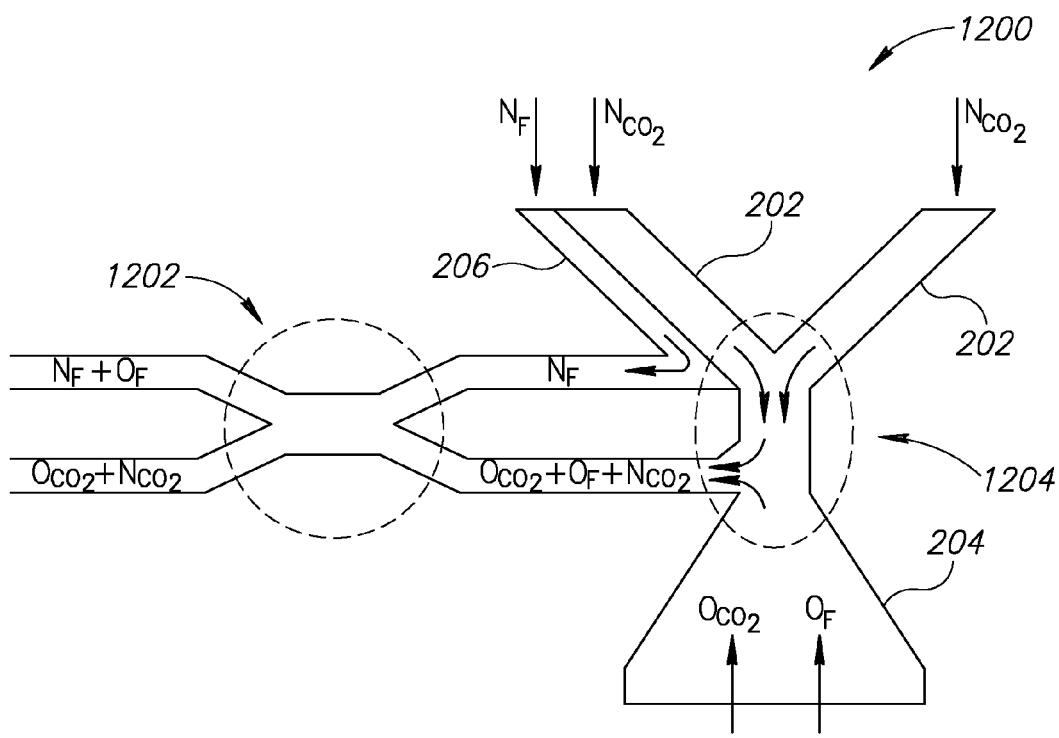
FIGS. 12, 13 and 14 show diagrams of gas flow inside an oral nasal cannula.

In an embodiment, a breath flow measurement sub-system includes a self-contained electronic pressure sensor embedded within a $CO_2$ sampling sub-system in such a way that cross-interference is mitigated or eliminated. Reference is now made to FIG. 12, which shows an oral nasal sampling cannula 1100, which includes many of the features of oral nasal sampling cannula 10 shown in FIGS. 1A-2C. Similar or identical features are shown with same reference numbers.

Oral nasal sampling cannula 1100 may include a self-contained electronic pressure sensor 1120 embedded within main body portion 12. Pressure sensor 1120 may be an essentially conventional electronic pressure sensor available on the market, of the kind that is adapted to measure pressure and transmit a reading, wirelessly or over an electrical wire, to an external device adapted to receive such result. Pressure sensor 1120 may be of such a size that enables its partial or complete embedding into main body portion 12.

A front end 1122 of pressure sensor 1120 may be positioned such that it is in fluid contact with Y junction 28, through a matching bore in the Y junction's wall. Front end 1122 is shown protruding into Y junction 28, but may nonetheless be implemented as being aligned with the wall of the Y junction or even withdrawn within the bore. Generally, as long as pressure sensor 1120 is positioned in fluid contact with Y junction 28 and in relative proximity to the Y junction, its readings may not be affected by the $CO_2$ sampling subsystem which collects its breath gasses through this junction. Better yet, positioning pressure sensor 1120 in the aforesaid location may allow it to sense and measure breath coming from both nasal prongs 18 and oral scoop element 22, whether the patient exhibits nasal breathing, oral breathing or both.

Pressure sensor 1120 may transmit its readings to an external device adapted to display and/or log breath flow readings. Such a device may optionally be implemented in a capnograph. The transmission may be wireless or through an electrical wire 1124 exiting pressure sensor 1120 towards the external device. Electrical wire 1124 may be functionally connected (not shown) to either oxygen delivery tube 36 or to exhaled breath collection tube 30, so that it does not add another loose wire to the system.

Reference is now made to FIG. 12, which shows a diagram of gas flow inside an oral nasal cannula 1200. Exhaled breath exits through the patient's nostrils and enters one or more nasal prongs 202 as well as breath flow measurement prong 206. Breath entering nasal prongs 202 is denoted $N_{CO_2}$ (Nasal $CO_2$), while breath entering or causing a pressure wave in breath flow measurement prong 206 is denoted $N_F$ (Nasal Flow).

From the lower side, oral breath enters an oral scoop 204, and the same breath is jointly used for both oral $CO_2$ ($O_{CO_2}$) collection and oral flow ($O_F$) measurement.

The $N_{CO_2}$, the $O_{CO_2}$ and the $O_F$ streams (where the $O_F$ may be a pressure wave rather than an actual stream) meet at essentially a Y junction 1204, whose unique design eliminates or at least mitigates $N_{CO_2}$ leakage through oral scoop 204, as well as $O_{CO_2}$ and $O_F$ leakage through nasal prongs 202.

From Y junction 1204, the $N_{CO_2}$, the $O_{CO_2}$ and the $O_F$ streams continue towards a mixture area 1202, in which they mix with the $N_F$ stream (or pressure wave) arriving from breath flow measurement prong 206. Following mixture area 1202, a first tube continues towards a flow measurement device and carries $N_F$ and $O_F$, while a second tube continues towards a capnograph and transports $N_{CO_2}$ and $O_{CO_2}$.

Mixture area 1202 may ensure that breath collected through all of nasal prongs 202, breath flow measurement prong 206 and oral scoop 204 participate in the capnographic $CO_2$ measurement and the flow measurement.

Figure 13:
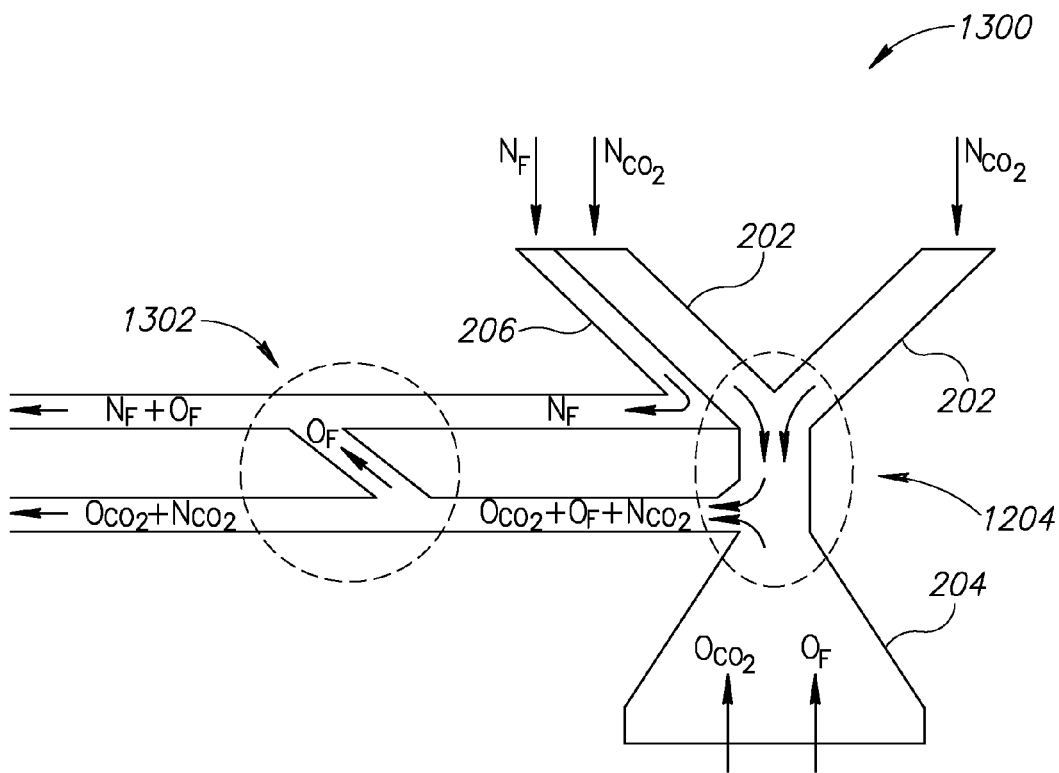

FIG. 13 shows another diagram of gas flow inside an oral nasal cannula 1300, wherein the mixture area feature is designed differently. Instead of joining and splitting the steams as in mixture area 1202 of FIG. 12, here a mixture area 1302 includes a passageway allowing $O_F$ to propagate from the Y junction area into the tube extending towards the flow measurement device.

Similarly, as will be understood by those of skill in the art, a mixture area may be designed in any manner functionally adapted to ensure that virtually all of the breath collected for $CO_2$ and flow measurement purposes receives proper representation at the final, measurement devices.

Figure 14:
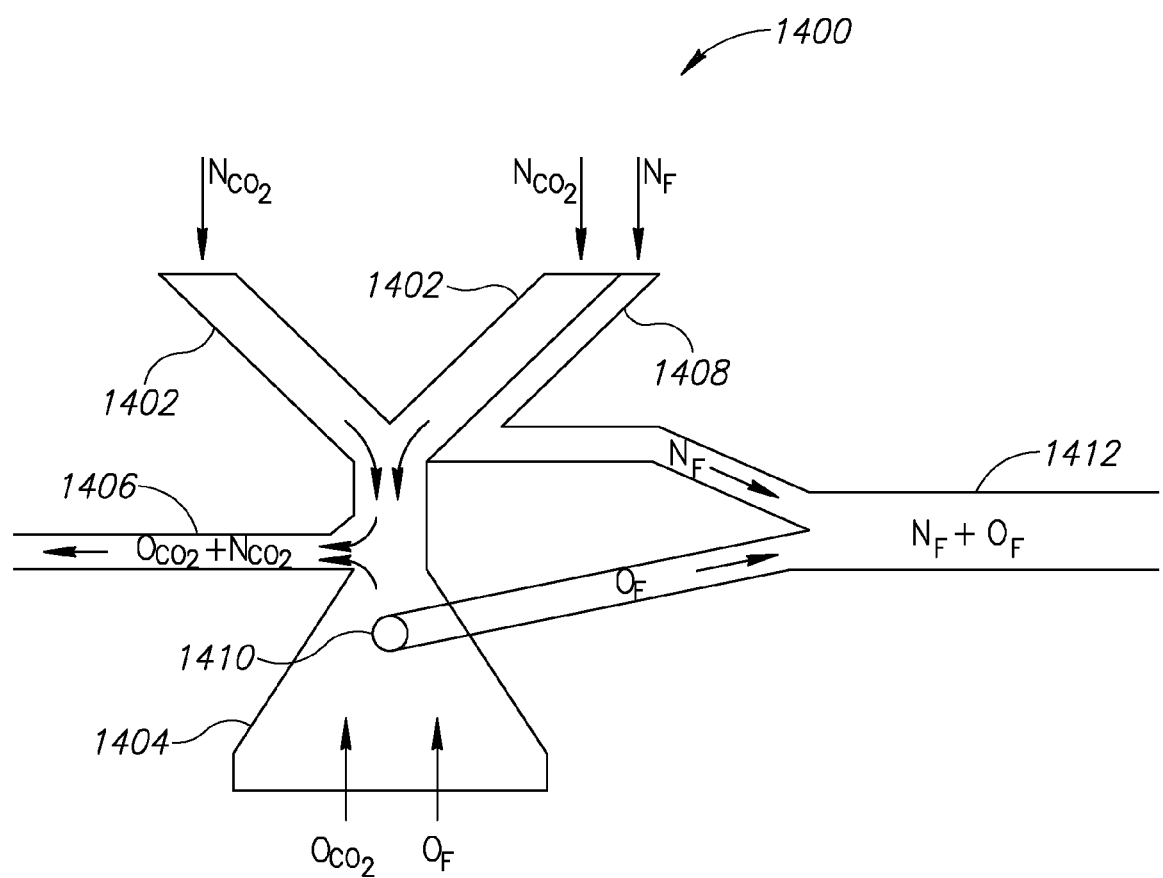

Reference is now made to FIG. 14, which shows yet another diagram of gas flow inside an oral nasal cannula 1400. Here, $N_{CO_2}$ and $N_F$ may be collected through nasal prongs 1402 and breath flow measurement prong 1408, respectively, similar to FIGS. 12 and 13. However, instead of having a mixture area, $O_F$ and $O_{CO_2}$ collected through an oral scoop 1404 may be separated early on, optionally at en exit port 1410 located in or near the scoop, such as right below the Y junction. From there, the $O_F$ may be joined with the $N_F$ and continue in a first tube 1412 towards a flow measurement device. The $O_{CO_2}$ be joined with the $N_{CO_2}$ at the Y junction, and the two of them may continue, through a second tube 1406, towards a capnograph.

This is yet another example of how a flow measurement sub-system, here including breath flow measurement prong 1408, exit port 1410 and first tube 1412, may be advantageously integrated with a $CO_2$ collection sub-system, here including nasal prongs 1402, oral scoop 1404 and second tube 1406.

Further Aspects of an Oral-Nasal Cannula System

A further aspect relates to the design of a single cannula which can be connected to both a Capnograph and a traditional breath flow-meter simultaneously, without each parameter interfering with the other. (Note, the flow meter can be part of the capnograph, since the basic part is an appropriate pressure sensor, the electronics and processing is often common to both CO2 and flow.)

The cannula design provides oral nasal $CO_2$ sampling of the same level as realized to date with existing $CO_2$ sampling cannula. The flow section provides patterns for both oral and nasal breathing that are at least as good as those received with standard breath flow cannula and should try to correct those issues defined above (poor oral flow).

Design Characteristics:

The combination of flow with $CO_2$ sampling does not make the cannula substantially more bulky, meaning it is not simply a piggyback solution.

The flow measurements (i.e. pressure line) is not essentially influenced (measurably) by fluctuations caused by the pump used for sampling the $CO_2$. (Hence the pressure line to the flow-meter and sampling line for the $CO_2$ are not common to the greatest extent possible). Note, if the pressure and sampling line would be common, then not only would there be interference from the pump, but also the small pressure changes being detected and used for flow measurement would be sitting on a the much larger pressure drop caused by the restriction of the sampling line acting against the pump, where this pressure drop would be fluctuating from time to time because of partial blockages caused by liquids being sucked into the line.

It is preferred that the oral prong of the cannula be common to both and collect both the flow and $CO_2$ sample in an optimal manner, without either compromising the other. Alternatively, oral collection may be common (such as using one scoop or prong), and the separation may be done essentially at an end of the scoop/prong (such as around area 230 shown in FIG. 10).

It is explained above why the optimal design should include a single junction between the oral and nasal sampling prongs, while on the other hand, when pressure is being measured, such a single junction, would lend itself to losing a major part of the pressure signal. In other words, when pressure is created at the nasal prongs, caused by nasal breathing, the pressure increase will fall (and be mainly lost) by escaping out via the oral prong, via the single junction, and will not be transmitted optimally along the pressure (flow) line which runs to the flow meter. The oral-nasal cannula system described here, advantageously deals with this issue.

When using the cannula for flow and $CO_2$ sampling outside the sleep lab, i.e. in critical care or sedation, where it is believed that also the double parameter will provide better patient monitoring, it may be necessary to also include a means for $O_2$ delivery, which when being delivered not interfere with the pressure measurements.

Reference is made back to FIG. 10. The sampling and flow (pressure) tubing divide (as will be explained) immediately after exiting the cannula blank (the cannula blank as defined herein includes only the sampling prongs, the junction and a small length of conduit ~2 cm, for connecting between the junction and sampling tube).

For optimal oral nasal $CO_2$ sampling, the oral prong is made with a large collecting funnel (inlet), where as the nasal prongs are made with narrow collectors (inlets). This is because the pressure created by the breath via the mouth is much weaker than that created via the nostrils, a result of the relative orifice sizes and body physiology. Further, when $O_2$ is delivered to the nose, narrower nasal prongs are preferred; in order to prevent $O_2$ that is simultaneously delivered, to return back through these prongs and consequently diluting the $CO_2$ sample.

Because of these constraints in the basic design for $CO_2$ sampling, the following issue occurs: When exhaling via the nose the pressure of the breath that is conducted into the nasal prong can easily escape via the much larger opening of the oral prong, and is damped considerably before passing along the long flow tubing connected with the flow meter. On the other hand, when breathing via the oral prong, the narrower nasal prongs provide a restriction, and the pressure signal collected is dampened much less.

For this reason, we use separate nasal prongs for sampling and flow (pressure), and add at least one separate nasal prong for pressure sensing along side one of the nasal $CO_2$ sampling prongs (optionally the prong that is on the other side to the collecting conduit). On the other hand, we may retain a common $CO_2$/pressure oral prong. Note, since the nasal prongs are anyway narrow, having two separate prongs is possible, but on the other hand the oral prong must be as large as possible for oral collection, and hence two separate oral prongs would only compete with each other for the same space.

As mentioned, it is in our interest that the flow and sampling line are kept to a minimum as a common line, and that we wish to avoid a "Y" junction design for the flow line.

Experimental Results

Three healthy patients were tested using a Capnograph and a breath flow meter. As a reference, the breath flow meter was used to evaluate what pattern could be realized with a standard system.

TABLE 1

Signal strength of flow pattern for oral and nasal breathing

| Breath Flow Cannula | Patient | Signal Strength | |
|---|---|---|---|
| | | Nasal Breathing | Oral Breathing |
| Breath flow meter | 1 | 2 | 2 |
| Standard Cannula | 2 | 2 | 0.5 |

TABLE 1-continued

Signal strength of flow pattern for oral and nasal breathing

| Breath Flow Cannula | Patient | Signal Strength | |
|---|---|---|---|
| | | Nasal Breathing | Oral Breathing |
| (Reference) | 3 | 5 | 5.7 |
| | Average | 3 | 2.7 |
| Single CO2/Flow cannula | 1 | 5 | 3.5 |
| | 2 | 3 | 1.5 |
| | 3 | 5.3 | 8 |
| | Average | 4.4 | 4.3 |

TABLE 2

$CO_2$ readings and flow measurements collected together with $O_2$ delivery

| Breath Flow Cannula | Patient | EtCO2 mmHg | | | |
|---|---|---|---|---|---|
| | | Nasal Breathing | | Oral Breathing | |
| | | 0 L/min | 3 L/min | 0 L/min | 3 L/min |
| single CO2/Flow cannula | 1 | 37 | 36 | 36 | 35 |
| | 2 | 39 | 37 | 33 | 30 |
| | 3 | 34 | 33 | 33 | 32 |
| | Average | 36 | 34 | 34 | 32.5 |

The $CO_2$ results shown in table 2 are very similar to standard sampling and no substantial effect on the $CO_2$ readings is noticed at 3 L/min. Neither was there any change to the flow patterns.

While a number of exemplary aspects and embodiments have been discussed above, those of skill in the art will recognize certain modifications, permutations, additions and sub-combinations thereof. It is therefore intended that the following appended claims and claims hereafter introduced be interpreted to include all such modifications, permutations, additions and sub-combinations as are within their true spirit and scope.

In the description and claims of the application, each of the words "comprise" "include" and "have", and forms thereof, are not necessarily limited to members in a list with which the words may be associated.

What we claim is:

1. An oral-nasal cannula configured for simultaneous, essentially interference-free carbon dioxide ($CO_2$) sampling and flow measurement of oral and nasal breath, the cannula comprising:
    a main body portion comprising:
        two nasal prongs for directing nasal breath for $CO_2$ sampling ($N_{CO2}$);
        a third nasal prong for directing nasal breath for flow measurement ($N_F$);
        an oral scoop for directing oral breath for both oral flow measurement ($O_F$) and oral $CO_2$ sampling ($O_{CO2}$);
        a first junction formed within said main body portion, above said oral scoop, said first junction configured to join said $O_{CO2}$ obtained from said scoop with said $N_{CO2}$ obtained from said two nasal prongs;
    a breath collection bore configured to receive said $N_{CO2}$ and $O_{CO2}$ from said first junction; and
    a second junction formed outside said main body portion and configured to join said $O_F$ with said $N_F$ so as to essentially prevent fluid flow connection between said $N_F$ and said $O_F$ within said main body portion.

2. The cannula of claim 1, further comprising an oral exit port exiting from said oral scoop at an upper end of said scoop.

3. The cannula of claim 1, further comprising an oxygen delivery outlet.

4. The cannula of claim 1, wherein said second junction is further configured to join said first junction is further configured to join said $O_{CO2}$ and said $N_{CO2}$ with said $O_F$.

5. An oral-nasal cannula configured for simultaneous, essentially interference-free carbon dioxide ($CO_2$) sampling and flow measurement of oral and nasal breath, the cannula comprising:
   a main body portion comprising:
      an oral scoop for directing oral breath for $CO_2$ sampling ($O_{CO2}$) and flow measurement ($O_F$);
      two nasal prongs for directing nasal breath for $CO_2$ sampling ($N_{CO2}$);
      a third nasal prong for directing nasal breath for flow measurement ($N_F$);
      a first junction formed within said main body portion, above said oral scoop, said first junction configured to join said $O_{CO2}$, said $O_F$ and said $N_{CO2}$; and
      a second junction formed outside said main body portion and configured to join said $O_F$ with said $N_F$ so as to essentially prevent fluid flow connection between said $N_F$ and said and said $O_F$ within said main body portion.

6. The oral-nasal cannula of claim 5, wherein interference-free carbon dioxide ($CO_2$) sampling and flow measurement is achieved by virtue of early separation of exhaled nasal breath for $CO_2$ sampling and exhaled nasal breath for flow measurement.

7. The oral-nasal cannula of claim 5, wherein interference-free carbon dioxide ($CO_2$) sampling and flow measurement is achieved by virtue of early separation of exhaled oral breath for $CO_2$ sampling and exhaled oral breath for flow measurement.

8. The oral-nasal cannula of claim 5, further comprising an oxygen outlet being in fluid segregation from said $CO_2$ sampling and said breath flow measurement, such that interference to said CO2 sampling sub-system and said breath flow measurement sub-system is essentially prevented.

9. A method for sampling carbon dioxide ($CO_2$) and measuring breath flow, essentially without cross-interference, the method comprising:
   directing nasal breath for $CO_2$ sampling ($N_{CO2}$) obtained from two nasal prongs;
   directing oral breath for $CO_2$ sampling ($O_{CO2}$) obtained from an oral scoop, wherein said $O_{CO2}$ is joined with said $N_{CO2}$ at a junction formed within said main body portion, above said oral scoop
   directing nasal breath for breath flow measurement ($N_F$) from a third nasal prong; and
   directing oral breath for flow measurement ($O_F$) from said oral scoop, wherein said $O_F$ from said oral scoop is joined with said $N_F$ from said third prong at a second junction outside said main body portion, so as to essentially prevent fluid flow connection between said $N_F$ and said $O_F$ within said main body portion.

10. The method of claim 9, further comprising $CO_2$ analysis by a capnograph, and breath flow measurement by a flow meter.

11. The method of claim 10, wherein the $CO_2$ analysis and the breath flow measurement are being conducted simultaneously.

* * * * *